(12) United States Patent
McMillan

(10) Patent No.: US 6,562,800 B1
(45) Date of Patent: May 13, 2003

(54) USE OF IMMUNOPOTENTIATING SEQUENCES FOR INDUCING IMMUNE RESPONSE

(75) Inventor: Minnie McMillan, Bradbury, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 09/430,470

(22) Filed: Oct. 29, 1999

Related U.S. Application Data

(60) Provisional application No. 60/106,506, filed on Oct. 30, 1998.

(51) Int. Cl.[7] .................. A61K 48/00; C12N 15/00; C07H 21/04
(52) U.S. Cl. .................. 514/44; 435/320.1; 536/23.1; 536/23.5; 536/23.4
(58) Field of Search .................. 435/320.1; 514/44; 536/23.5

(56) References Cited

U.S. PATENT DOCUMENTS 5,846,546 A * 12/1998 Hurwitz et al. .......... 424/202.1
5,935,568 A * 8/1999 Dow et al. ............... 424/93.21

FOREIGN PATENT DOCUMENTS

WO  WO 97/15594  * 10/1996
WO  99-29728     * 12/1997

OTHER PUBLICATIONS

Shiver et al., Humoral and Cellular Immunities Elicited by HIV–1 DNA Vaccination, Journal of Pharmaceuitical Science, Dec. 1996, vol. 85, No. 12, pp. 1317–1324.*

Kim et al., Modulation of amplitude and direction of in vivo immune responses by co–administration of cytokine gene expression cassettes with DNA immunogens, 1998, Eur. J. Immunol., vol. 28, p. 1089–1103.*

Wu et al., Engineering and intreacellular pathway for major histocompatibiliy complex class II presentation of antigens, Dec. 1995, Proc. Natl. Acad. Sci., p. 11671–11675.*

Lee et al., Major histocompatibility complex class I presentation of exogenous soluble turmor antigen fused to the B–fragment of Shiga toxin, 1998, Eur. J. Immunol., vol. 28, pp. 27226–2737.*

Denis et al., Vaccinatin with Plasmid DNA Encoding Mycobacterial Antigen 85a Stimulates a CD4+ . . . , Apr. 1998, Infection and Immunity, vol. 66, No. 4, pp. 1527–1533.*

An et al., A Multuvalent Minigene Vaccine, Containing B–Cell, Cytotoxic T–Lymphocyte, and Th Epitopes . . . , Mar. 1997, Journal of Virology, vol. 71, No. 3, pp. 2292–2302.*

Nathason et al., Biological Consideration in the Development of a Human Immunodeficiency Virus Vaccine, pp. 579–589.*

Aderson et al., Human gene therapy, Apr. 30, 1988, vol. 392, Nature, pp. 25–30.*

McClusklie et al., Route and Method of Delivery of DNA Vaccine Influence Immune Responses in Mice and Non–Human Primate Molecular Medicine, 1999, vol. 5, pp. 287–300.*

Bonecchi, R. et al., "Differential Expression of Chemokine Receptors and Chemotactic Responsiveness of Type 1T Helper Cells (TH1s) and Th2s," J. Exp. Med., The Rockfeller University Press, vol. 187, No. 1, Jan. 5, 1998, pp. 129–134.

Siveke, J. et al., "Cutting Edge: T Helper 1 and T Helper 2 Cells Respond Differentially to Chemokines," The American Association of Immunologists, 1998, pp. 550–554.

Zingoni, A. et al., "Cutting Edge: The Chemokine Receptor CCR8 is Preferentially Expressed in Th2 But Not Th1 Cells[1,2]," The American Association of Immunologists, 1998, pp. 547–551.

Mellado, M. et al., "HIV–1 Envelope Protein GP120 Triggers a Th2 Response in Mice that Shifts to Th1 in the Presence of Human Growth Hormone," Eisevier Science Ltd., vol. 15, No. 11, 1998, pp. 1111–1115.

Baggiolini, M., "Chemokines and Leukocyte Traffic," Nature, vol. 392, Apr. 9, 1998, pp. 565–568.

Pamer, E. et al., "Mechanisms of MHC Class I–Restricted Antigen Processing," Annu. Rev. Immunol., 1998, pp. 323–358.

* cited by examiner

Primary Examiner—Jeffrey Fredman
Assistant Examiner—Jon E Angell
(74) Attorney, Agent, or Firm—Bingham McCutchen LLP

(57) ABSTRACT

The present invention provides an immunogenic composition comprising a DNA expression vector encoding both an immunopotentiating chemokine sequence as well as an immunogenic polypeptide sequence. Immunogenic polypeptide sequences are those of infectious agents or of cancerous cells. Also provided are methods of manufacturing various immunogenic compositions, and methods of using such compositions to treat cancer and infectious disease.

17 Claims, 19 Drawing Sheets

A.

| hydrophobic leader synthesis into the ER | gp 120(315-329) T$_C$ epitope | spacer longer mRNA | KDEL ER retention |

SAK

| hydrophobic leader synthesis into the ER | MIP-1β chemotactic | gp 120(315-329) T$_C$ epitope | spacer longer mRNA | KDEL ER retention |

MIP-1β-SAK

| hydrophobic leader synthesis into the ER | MIP-1β chemotactic | gp 120(315-329) $T_C$ epitope | spacer longer mRNA | KDEL ER retention |

| hydrophobic leader synthesis into the ER | MIP-1β chemotactic | gp 120(315-329) $T_C$ epitope | OVA(317-342) $T_H$ epitope | hydrophobic membrane-spanning | YXXZ to endosome | di-leucine to endosome |

FIG. 9B

CMV/MIP-1b/p18/OVA/TMYZLL Sequence

```
           10         20         30         40         50
  1234567890 1234567890 1234567890 1234567890 1234567890

BstEII
▼
GGTGACCGGA GATCTGCCGC CACCATGGGG GCGATGGCTC CGCGCACGCT    50
CCACTGGCCT CTAGACGGCG GTGGTACCCC CGCTACCGAG GCGCGTGCGA
GlyAspArgA rgSerAlaAl aThrMetGly AlaMetAlaP roArgThrLe
ValThrGly  AspLeuProP roProTrpGl yArgTrpLeu ArgAlaArgC
  ...ProGl uIleCysArg HisHisGlyG lyAspGlySe rAlaHisAla

NotI
                      ▼
GCTCCTGCTG CTGGCGGCCG CCCTGGCCCC GACTCAGACC CGCGCGGCGC   100
CGAGGACGAC GACCGCCGGC GGGACCGGGG CTGAGTCTGG GCGCGCCGCG
uLeuLeuLeu LeuAlaAlaA laLeuAlaPr oThrGlnThr ArgAlaAlaP
ysSerCysCy sTrpArgPro ProTrpProA rgLeuArgPr oAlaArgArg
AlaProAlaA laGlyGlyAr gProGlyPro AspSerAspP roArgGlyAl

ApaI
                                 ▼
CAATGGGCTC TGACCCTCCC ACTTCCGGGC CCGAGTATTG GGAGCGTATC   150
GTTACCCGAG ACTGGGAGGG TGAAGGCCCG GGCTCATAAC CCTCGCATAG
roMetGlySe rAspProPro ThrSerGlyP roGluTyrTr pGluArgIle
GlnTrpAlaL euThrLeuPr oLeuProGly ProSerIleG lySerValSe
aAsnGlyLeu ...ProSerH isPheArgAl aArgValLeu GlyAlaTyrP

AgeI
                                            ▼
CAGAGAGGAC CAGGGAGAGC ATTTGTTACA ATAGGTAAAA CCGGTAGCGC   200
GTCTCTCCTG GTCCCTCTCG TAAACAATGT TATCCATTTT GGCCATCGCG
GlnArgGlyP roGlyArgAl aPheValThr IleGlyLysT hrGlySerAl
rArgGluAsp GlnGlyGluH isLeuLeuGl n...ValLys ProValAlaG
roGluArgTh rArgGluSer IleCysTyrA snArg...As nArg...Arg

AGAGAGCCTG AAGATATCTC AAGCTGTCCA TGCAGCACAT GCAGAAATCA   250
TCTCTCGGAC TTCTATAGAG TTCGACAGGT ACGTCGTGTA CGTCTTTAGT
aGluSerLeu LysIleSerG lnAlaValHi sAlaAlaHis AlaGluIleA
lnArgAla.. .ArgTyrLeu LysLeuSerM etGlnHisMe tGlnLysSer
ArgGluProG luAspIleSe rSerCysPro CysSerThrC ysArgAsnGl
```

Figure 10A

CMV/MIP-1b/p18/OVA/TMYZLL Sequence

```
         10         20         30         40         50
1234567890 1234567890 1234567890 1234567890 1234567890
                      AflII
                        ▼
ATGAAGCAGG CAGAGAGGTG CTTAAGTGGG AGCCTCCTCC GTCCACTGAC   300
TACTTCGTCC GTCTCTCCAC GAATTCACCC TCGGAGGAGG CAGGTGACTG
snGluAlaGl yArgGluVal LeuLysTrpG luProProPr oSerThrAsp
MetLysGlnA laGluArgCy sLeuSerGly SerLeuLeuA rgProLeuTh
n...SerArg GlnArgGlyA la...ValGl yAlaSerSer ValHis...L

TCTTACATGG TGATCGTTGC TGTTCTGGGT GTCCTTGGAG CTATGGCCAT   350
AGAATGTACC ACTAGCAACG ACAAGACCCA CAGGAACCTC GATACCGGTA
SerTyrMetV alIleValAl aValLeuGly ValLeuGlyA laMetAlaIl
rLeuThrTrp ...SerLeuL euPheTrpVa lSerLeuGlu LeuTrpProS
euLeuHisGl yAspArgCys CysSerGlyC ysProTrpSe rTyrGlyHis

NheI
                                              ▼
CATTGGAGCT GTGGTGGCTT TTGTGATGAA GAGAAGGAGA GCTAGCCACG   400
GTAACCTCGA CACCACCGAA AACACTACTT CTCTTCCTCT CGATCGGTGC
eIleGlyAla ValValAlaP heValMetLy sArgArgArg AlaSerHisA
erLeuGluLe uTrpTrpLeu Leu......A rgGluGlyGl uLeuAlaThr
HisTrpSerC ysGlyGlyPh eCysAspGlu GluLysGluS er...ProAr

CCGGCTATCA GACCATAGTG TCCTTCCATG ATGACAGCGA CGAAGACCTC   450
GGCCGATAGT CTGGTATCAC AGGAAGGTAC TACTGTCGCT GCTTCTGGAG
laGlyTyrGl nThrIleVal SerPheHisA spAspSerAs pGluAspLeu
ProAlaIleA rgPro...Cy sProSerMet MetThrAlaT hrLysThrSe
gArgLeuSer AspHisSerV alLeuPro.. ....GlnArg ArgArgProL

BstEII       SacII
                                  ▼            ▼
TTACACATAT AGATAACCAC TGCAGTGGAT CGGGTGACCA TCGCCGCGG    499
AATGTGTATA TCTATTGGTG ACGTCACCTA GCCCACTGGT AGCGGCGCC
LeuHisIle. ..IleThrTh rAlaValAsp ArgValThrI leAlaAla
rTyrThrTyr Arg...ProL euGlnTrpIl eGly...Pro SerProArg
euThrHisIl eAspAsnHis CysSerGlyS erGlyAspHi sArgArg
```

Figure 10B

CMV/MIP-3b/p18/OVA/TMYZLL Sequence

```
               10         20         30         40         50
        1234567890 1234567890 1234567890 1234567890 1234567890
        BstEII
        ▼
        GGTGACCGGA GATCTGCCGC CACCATGGGG GCGATGGCTC CGCGCACGCT     50
        CCACTGGCCT CTAGACGGCG GTGGTACCCC CGCTACCGAG GCGCGTGCGA
        GlyAspArgA rgSerAlaAl aThrMetGly AlaMetAlaP roArgThrLe
         ValThrGly AspLeuProP roProTrpGl yArgTrpLeu ArgAlaArgC
           ...ProGl uIleCysArg HisHisGlyG lyAspGlySe rAlaHisAla

NotI
                          ▼
        GCTCCTGCTG CTGGCGGCCG CCCTGGCCCC GACTCAGACC CGCGCGGGTG    100
        CGAGGACGAC GACCGCCGGC GGGACCGGGG CTGAGTCTGG GCGCGCCCAC
        uLeuLeuLeu LeuAlaAlaA laLeuAlaPr oThrGlnThr ArgAlaGlyA
        ySerCysCy sTrpArgPro ProTrpProA rgLeuArgPr oAlaArgVal
        AlaProAlaA laGlyGlyAr gProGlyPro AspSerAspP roArgGlyCy

ApaI
                                    ▼
        CTAATGATGC GGAAGACGGG CCCGAGTATT GGGAGCGTAT CCAGAGAGGA    150
        GATTACTACG CCTTCTGCCC GGGCTCATAA CCCTCGCATA GGTCTCTCCT
        laAsnAspAl aGluAspGly ProGluTyrT rpGluArgIl eGlnArgGly
        LeuMetMetA rgLysThrGl yProSerIle GlySerValS erArgGluAs
        s......Cys GlyArgArgA laArgValLe uGlyAlaTyr ProGluArgT

AgeI
                                              ▼
        CCAGGGAGAG CATTTGTTAC AATAGGTAAA ACCGGTAGCG CAGAGAGCCT    200
        GGTCCCTCTC GTAAACAATG TTATCCATTT TGGCCATCGC GTCTCTCGGA
        ProGlyArgA laPheValTh rIleGlyLys ThrGlySerA laGluSerLe
        pGlnGlyGlu HisLeuLeuG ln...ValLy sProValAla GlnArgAla.
        hrArgGluSe rIleCysTyr AsnArg...A snArg...Ar gArgGluPro

GAAGATATCT CAAGCTGTCC ATGCAGCACA TGCAGAAATC AATGAAGCAG    250
        CTTCTATAGA GTTCGACAGG TACGTCGTGT ACGTCTTTAG TTACTTCGTC
        uLysIleSer GlnAlaValH isAlaAlaHi sAlaGluIle AsnGluAlaG
        ..ArgTyrLe uLysLeuSer MetGlnHisM etGlnLysSe rMetLysGln
        GluAspIleS erSerCysPr oCysSerThr CysArgAsnG ln...SerAr
```

Figure 11A.

CMV/MIP-3b/p18/OVA/TMYZLL Sequence

```
         10         20         30         40         50
1234567890 1234567890 1234567890 1234567890 1234567890
           AflII
                ▼
GCAGAGAGGT GCTTAAGTGG GAGCCTCCTC CGTCCACTGA CTCTTACATG    300
CGTCTCTCCA CGAATTCACC CTCGGAGGAG GCAGGTGACT GAGAATGTAC
lyArgGluVa lLeuLysTrp GluProProP roSerThrAs pSerTyrMet
AlaGluArgC ysLeuSerGl ySerLeuLeu ArgProLeuT hrLeuThrTr
gGlnArgGly Ala...ValG lyAlaSerSe rValHis... LeuLeuHisG

GTGATCGTTG CTGTTCTGGG TGTCCTTGGA GCTATGGCCA TCATTGGAGC    350
CACTAGCAAC GACAAGACCC ACAGGAACCT CGATACCGGT AGTAACCTCG
ValIleValA laValLeuGl yValLeuGly AlaMetAlaI leIleGlyAl
p...SerLeu LeuPheTrpV alSerLeuGl uLeuTrpPro SerLeuGluL
lyAspArgCy sCysSerGly CysProTrpS erTyrGlyHi sHisTrpSer

NheI
                                 ▼
TGTGGTGGCT TTTGTGATGA AGAGAAGGAG AGCTAGCCAC GCCGGCTATC    400
ACACCACCGA AAACACTACT TCTCTTCCTC TCGATCGGTG CGGCCGATAG
aValValAla PheValMetL ysArgArgAr gAlaSerHis AlaGlyTyrG
euTrpTrpLe uLeu...... ArgGluGlyG luLeuAlaTh rProAlaIle
CysGlyGlyP heCysAspGl uGluLysGlu Ser...ProA rgArgLeuSe

AGACCATAGT GTCCTTCCAT GATGACAGCG ACGAAGACCT CTTACACATA    450
TCTGGTATCA CAGGAAGGTA CTACTGTCGC TGCTTCTGGA GAATGTGTAT
lnThrIleVa lSerPheHis AspAspSerA spGluAspLe uLeuHisIle
ArgPro...C ysProSerMe tMetThrAla ThrLysThrS erTyrThrTy
rAspHisSer ValLeuPro. .....GlnAr gArgArgPro LeuThrHisI

BstEII       SacII
                       ▼             ▼
TAGATAACCA CTGCAGTGGA TCGGGTGACC ATCGCCGCGG              490
ATCTATTGGT GACGTCACCT AGCCCACTGG TAGCGGCGCC
...IleThrT hrAlaValAs pArgValThr IleAlaAla
rArg...Pro LeuGlnTrpI leGly...Pr oSerProArg
leAspAsnHi sCysSerGly SerGlyAspH isArgArg
```

Figure 11B.

CMV/TCA-3/p18/OVA/TMYZLL Sequence

```
            10         20         30         40         50
       1234567890 1234567890 1234567890 1234567890 1234567890

BstEII
  ▼
  GGTGACCGGA GATCTGCCGC CACCATGGGG GCGATGGCTC CGCGCACGCT    50
  CCACTGGCCT CTAGACGGCG GTGGTACCCC CGCTACCGAG GCGCGTGCGA
  GlyAspArgA rgSerAlaAl aThrMetGly AlaMetAlaP roArgThrLe
   ValThrGly AspLeuProP roProTrpGl yArgTrpLeu ArgAlaArgC
     ...ProGl uIleCysArg HisHisGlyG lyAspGlySe rAlaHisAla

NotI
                       ▼
  GCTCCTGCTG CTGGCGGCCG CCCTGGCCCC GACTCAGACC CGCGCGAAGA    100
  CGAGGACGAC GACCGCCGGC GGGACCGGGG CTGAGTCTGG GCGCGCTTCT
  uLeuLeuLeu LeuAlaAlaA laLeuAlaPr oThrGlnThr ArgAlaLysS
  ySerCysCy sTrpArgPro ProTrpProA rgLeuArgPr oAlaArgArg
  AlaProAlaA laGlyGlyAr gProGlyPro AspSerAspP roArgGluGl

ApaI
                            ▼
  GCATGCTTAC GGTCTCCAAT AGCGGGCCCG AGTATTGGGA GCGTATCCAG    150
  CGTACGAATG CCAGAGGTTA TCGCCCGGGC TCATAACCCT CGCATAGGTC
  erMetLeuTh rValSerAsn SerGlyProG luTyrTrpGl uArgIleGln
  AlaCysLeuA rgSerProIl eAlaGlyPro SerIleGlyS erValSerAr
  uHisAlaTyr GlyLeuGln. ..ArgAlaAr gValLeuGly AlaTyrProG

AgeI
                                  ▼
  AGAGGACCAG GGAGAGCATT TGTTACAATA GGTAAAACCG GTAGCGCAGA    200
  TCTCCTGGTC CCTCTCGTAA ACAATGTTAT CCATTTTGGC CATCGCGTCT
  ArgGlyProG lyArgAlaPh eValThrIle GlyLysThrG lySerAlaGl
  gGluAspGln GlyGluHisL euLeuGln.. .ValLysPro ValAlaGlnA
  luArgThrAr gGluSerIle CysTyrAsnA rg...AsnAr g...ArgArg

GAGCCTGAAG ATATCTCAAG CTGTCCATGC AGCACATGCA GAAATCAATG    250
  CTCGGACTTC TATAGAGTTC GACAGGTACG TCGTGTACGT CTTTAGTTAC
  uSerLeuLys IleSerGlnA laValHisAl aAlaHisAla GluIleAsnG
  rgAla...Ar gTyrLeuLys LeuSerMetG lnHisMetGl nLysSerMet
  GluProGluA spIleSerSe rCysProCys SerThrCysA rgAsnGln..
```

Figure 12A.

CMV/TCA-3/p18/OVA/TMYZLL Sequence

```
         10         20         30         40         50
1234567890 1234567890 1234567890 1234567890 1234567890
                AflII
                  ▼
AAGCAGGCAG AGAGGTGCTT AAGTGGGAGC CTCCTCCGTC CACTGACTCT    300
TTCGTCCGTC TCTCCACGAA TTCACCCTCG GAGGAGGCAG GTGACTGAGA
luAlaGlyAr gGluValLeu LysTrpGluP roProProSe rThrAspSer
LysGlnAlaG luArgCysLe uSerGlySer LeuLeuArgP roLeuThrLe
.SerArgGln ArgGlyAla. ..ValGlyAl aSerSerVal His...LeuL

TACATGGTGA TCGTTGCTGT TCTGGGTGTC CTTGGAGCTA TGGCCATCAT    350
ATGTACCACT AGCAACGACA AGACCCACAG GAACCTCGAT ACCGGTAGTA
TyrMetValI leValAlaVa lLeuGlyVal LeuGlyAlaM etAlaIleIl
uThrTrp... SerLeuLeuP heTrpValSe rLeuGluLeu TrpProSerL
euHisGlyAs pArgCysCys SerGlyCysP roTrpSerTy rGlyHisHis

NheI
                                      ▼
TGGAGCTGTG GTGGCTTTTG TGATGAAGAG AAGGAGAGCT AGCCACGCCG    400
ACCTCGACAC CACCGAAAAC ACTACTTCTC TTCCTCTCGA TCGGTGCGGC
eGlyAlaVal ValAlaPheV alMetLysAr gArgArgAla SerHisAlaG
euGluLeuTr pTrpLeuLeu ......ArgG luGlyGluLe uAlaThrPro
TrpSerCysG lyGlyPheCy sAspGluGlu LysGluSer. ..ProArgAr

GCTATCAGAC CATAGTGTCC TTCCATGATG ACAGCGACGA AGACCTCTTA    450
CGATAGTCTG GTATCACAGG AAGGTACTAC TGTCGCTGCT TCTGGAGAAT
lyTyrGlnTh rIleValSer PheHisAspA spSerAspGl uAspLeuLeu
AlaIleArgP ro...CysPr oSerMetMet ThrAlaThrL ysThrSerTy
gLeuSerAsp HisSerValL euPro..... .GlnArgArg ArgProLeuT

BstEII      SacII
                                  ▼          ▼
CACATATAGA TAACCACTGC AGTGGATCGG GTGACCATCG CCGCGG        496
GTGTATATCT ATTGGTGACG TCACCTAGCC CACTGGTAGC GGCGCC
HisIle...I leThrThrAl aValAspArg ValThrIleA laAla
rThrTyrArg ...ProLeuG lnTrpIleGl y...ProSer ProArg
hrHisIleAs pAsnHisCys SerGlySerG lyAspHisAr gArg
```

Figure 12B.

CMV/SDF-1/p18/OVA/TMYZLL Sequence

```
        10         20         30         40         50
1234567890 1234567890 1234567890 1234567890 1234567890

BglII      NcoI
GGTGACCGGA GATCTGCCGC CACCATGGGG GCGATGGCTC CGCGCACGCT    50
CCACTGGCCT CTAGACGGCG GTGGTACCCC CGCTACCGAG GCGCGTGCGA
GlyAspArgA rgSerAlaAl aThrMetGly AlaMetAlaP roArgThrLe
 ValThrGly AspLeuProP roProTrpGl yArgTrpLeu ArgAlaArgC
  ...ProGl uIleCysArg HisHisGlyG lyAspGlySe rAlaHisAla

EagI
GCTCCTGCTG CTGGCGGCCG CCCTGGCCCC GACTCAGACC CGCGCGAAAC   100
CGAGGACGAC GACCGCCGGC GGGACCGGGG CTGAGTCTGG GCGCGCTTTG
uLeuLeuLeu LeuAlaAlaA laLeuAlaPr oThrGlnThr ArgAlaLysP
ysSerCysCy sTrpArgPro ProTrpProA rgLeuArgPr oAlaArgAsn
AlaProAlaA laGlyGlyAr gProGlyPro AspSerAspP roArgGluTh

ApaI
CAGTCAGCCT GAGCTACCGA GGGCCCGAGT ATTGGGAGCG TATCCAGAGA   150
GTCAGTCGGA CTCGATGGCT CCCGGGCTCA TAACCCTCGC ATAGGTCTCT
roValSerLe uSerTyrArg GlyProGluT yrTrpGluAr gIleGlnArg
GlnSerAla. ..AlaThrGl uGlyProSer IleGlySerV alSerArgGl
rSerGlnPro GluLeuProA rgAlaArgVa lLeuGlyAla TyrProGluA

AgeI
GGACCAGGGA GAGCATTTGT TACAATAGGT AAAACCGGTA GCGCAGAGAG   200
CCTGGTCCCT CTCGTAAACA ATGTTATCCA TTTTGGCCAT CGCGTCTCTC
GlyProGlyA rgAlaPheVa lThrIleGly LysThrGlyS erAlaGluSe
uAspGlnGly GluHisLeuL euGln...Va lLysProVal AlaGlnArgA
rgThrArgGl uSerIleCys TyrAsnArg. ..AsnArg.. .ArgArgGlu

EcoRV
CCTGAAGATA TCTCAAGCTG TCCATGCAGC ACATGCAGAA ATCAATGAAG   250
GGACTTCTAT AGAGTTCGAC AGGTACGTCG TGTACGTCTT TAGTTACTTC
rLeuLysIle SerGlnAlaV alHisAlaAl aHisAlaGlu IleAsnGluA
la...ArgTy rLeuLysLeu SerMetGlnH isMetGlnLy sSerMetLys
ProGluAspI leSerSerCy sProCysSer ThrCysArgA snGln...Se
```

Figure 13A.

CMV/SDF-1/p18/OVA/TMYZLL Sequence

```
         10         20         30         40         50
1234567890 1234567890 1234567890 1234567890 1234567890

AflII
CAGGCAGAGA GGTGCTTAAG TGGGAGCCTC CTCCGTCCAC TGACTCTTAC    300
GTCCGTCTCT CCACGAATTC ACCCTCGGAG GAGGCAGGTG ACTGAGAATG
laGlyArgGl uValLeuLys TrpGluProP roProSerTh rAspSerTyr
GlnAlaGluA rgCysLeuSe rGlySerLeu LeuArgProL euThrLeuTh
rArgGlnArg GlyAla...V alGlyAlaSe rSerValHis ...LeuLeuH

BalI
ATGGTGATCG TTGCTGTTCT GGGTGTCCTT GGAGCTATGG CCATCATTGG    350
TACCACTAGC AACGACAAGA CCCACAGGAA CCTCGATACC GGTAGTAACC
MetValIleV alAlaValLe uGlyValLeu GlyAlaMetA laIleIleGl
rTrp...Ser LeuLeuPheT rpValSerLe uGluLeuTrp ProSerLeuG
isGlyAspAr gCysCysSer GlyCysProT rpSerTyrGl yHisHisTrp

NheI       NaeI
AGCTGTGGTG GCTTTTGTGA TGAAGAGAAG GAGAGCTAGC CACGCCGGCT    400
TCGACACCAC CGAAAACACT ACTTCTCTTC CTCTCGATCG GTGCGGCCGA
yAlaValVal AlaPheValM etLysArgAr gArgAlaSer HisAlaGlyT
luLeuTrpTr pLeuLeu... ...ArgGluG lyGluLeuAl aThrProAla
SerCysGlyG lyPheCysAs pGluGluLys GluSer...P roArgArgLe

ATCAGACCAT AGTGTCCTTC CATGATGACA GCGACGAAGA CCTCTTACAC    450
TAGTCTGGTA TCACAGGAAG GTACTACTGT CGCTGCTTCT GGAGAATGTG
yrGlnThrIl eValSerPhe HisAspAspS erAspGluAs pLeuLeuHis
IleArgPro. ..CysProSe rMetMetThr AlaThrLysT hrSerTyrTh
uSerAspHis SerValLeuP ro......Gl nArgArgArg ProLeuThrH

PstI                          SacII
ATATAGATAA CCACTGCAGT GGATCGGGTG ACCATCGCCG CGG           493
TATATCTATT GGTGACGTCA CCTAGCCCAC TGGTAGCGGC GCC
Ile...IleT hrThrAlaVa lAspArgVal ThrIleAlaA la
rTyrArg... ProLeuGlnT rpIleGly.. .ProSerPro Arg
isIleAspAs nHisCysSer GlySerGlyA spHisArgAr g
```

Figure 13B.

CMV/Crg-2/SAK Sequence

```
         10         20         30         40         50
  1234567890 1234567890 1234567890 1234567890 1234567890
     BstEII
  ▼
  GATGGTGACC GGAGATCTGC CGCCACCATG GGGGCGATGG CTCCGCGCAC    50
  CTACCACTGG CCTCTAGACG GCGGTGGTAC CCCCGCTACC GAGGCGCGTG
  AspGlyAspA rgArgSerAl aAlaThrMet GlyAlaMetA laProArgTh
   MetValThr GlyAspLeuP roProProTr pGlyArgTrp LeuArgAlaA
      Trp...Pr oGluIleCys ArgHisHisG lyGlyAspGl ySerAlaHis

NotI
                          ▼
  GCTGCTCCTG CTGCTGGCGG CCGCCCTGGC CCCGACTCAG ACCCGCGCGA   100
  CGACGAGGAC GACGACCGCC GGCGGGACCG GGGCTGAGTC TGGGCGCGCT
  rLeuLeuLeu LeuLeuAlaA laAlaLeuAl aProThrGln ThrArgAlaI
  rgCysSerCy sCysTrpArg ProProTrpP roArgLeuAr gProAlaArg
  AlaAlaProA laAlaGlyGl yArgProGly ProAspSerA spProArgAs

ApaI
                                   ▼
  TCCCTCTCGC AAGGACGGTC AGAGGGCCCG AGTATTGGGA GCGTATCCAG   150
  AGGGAGAGCG TTCCTGCCAG TCTCCCGGGC TCATAACCCT CGCATAGGTC
  leProLeuAl aArgThrVal ArgGlyProG luTyrTrpGl uArgIleGln
  SerLeuSerG lnGlyArgSe rGluGlyPro SerIleGlyS erValSerAr
  pProSerArg LysAspGlyG lnArgAlaAr gValLeuGly AlaTyrProG

AGAGGACCAG GGAGAGCATT TGTTACAATA GGAAAAAACC TTCGAACCCT   200
  TCTCCTGGTC CCTCTCGTAA ACAATGTTAT CCTTTTTTGG AAGCTTGGGA
  ArgGlyProG lyArgAlaPh eValThrIle GlyLysAsnL euArgThrLe
  gGluAspGln GlyGluHisL euLeuGln.. .GluLysThr PheGluProC
  luArgThrAr gGluSerIle CysTyrAsnA rgLysLysPr oSerAsnPro

GCTCGGCTAC TACAACCAGT CGGCCGGCGG CACTCACACA CTGCAGAAGG   250
  CGAGCCGATG ATGTTGGTCA GCCGGCCGCC GTGAGTGTGT GACGTCTTCC
  uLeuGlyTyr TyrAsnGlnS erAlaGlyGl yThrHisThr LeuGlnLysA
  ysSerAlaTh rThrThrSer ArgProAlaA laLeuThrHi sCysArgArg
  AlaArgLeuL euGlnProVa lGlyArgArg HisSerHisT hrAlaGluGl
```

Figure 14A.

CMV/Crg-2/SAK Sequence

```
         10         20         30         40         50
1234567890 1234567890 1234567890 1234567890 1234567890

HindIII                    XbaI
ACGAGCTCTA AGCTTAGATA AGTAAAATTC GAGCTCTAGA T           291
TGCTCGAGAT TCGAATCTAT TCATTTTAAG CTCGAGATCT A
spGluLeu.. .Ala...Ile SerLysIleA rgAlaLeuAs p
ThrSerSerL ysLeuArg.. .ValLysPhe GluLeu...
yArgAlaLeu SerLeuAspL ys...AsnSe rSerSerArg
```

Figure 14B.

CMV/RANTES/SAK Sequence

```
        10         20         30         40         50
1234567890 1234567890 1234567890 1234567890 1234567890

BstEII
GATGGTGACC GGAGATCTGC CGCCACCATG GGGGCGATGG CTCCGCGCAC      50
CTACCACTGG CCTCTAGACG GCGGTGGTAC CCCCGCTACC GAGGCGCGTG
AspGlyAspA rgArgSerAl aAlaThrMet GlyAlaMetA laProArgTh
 MetValThr GlyAspLeuP roProProTr pGlyArgTrp LeuArgAlaA
  Trp...Pr oGluIleCys ArgHisHisG lyGlyAspGl ySerAlaHis

NotI
GCTGCTCCTG CTGCTGGCGG CCGCCCTGGC CCCGACTCAG ACCCGCGCGT     100
CGACGAGGAC GACGACCGCC GGCGGGACCG GGGCTGAGTC TGGGCGCGCA
rLeuLeuLeu LeuLeuAlaA laAlaLeuAl aProThrGln ThrArgAlaS
rgCysSerCy sCysTrpArg ProProTrpP roArgLeuAr gProAlaArg
AlaAlaProA laAlaGlyGl yArgProGly ProAspSerA spProArgVa

ApaI
CACCATATGG CTCGGACACC ACTCCCGGGC CCGAGTATTG GGAGCGTATC     150
GTGGTATACC GAGCCTGTGG TGAGGGCCCG GGCTCATAAC CCTCGCATAG
erProTyrGl ySerAspThr ThrProGlyP roGluTyrTr pGluArgIle
HisHisMetA laArgThrPr oLeuProGly ProSerIleG lySerValSe
lThrIleTrp LeuGlyHisH isSerArgAl aArgValLeu GlyAlaTyrP

CAGAGAGGAC CAGGGAGAGC ATTTGTTACA ATAGGAAAAA ACCTTCGAAC     200
GTCTCTCCTG GTCCCTCTCG TAAACAATGT TATCCTTTTT TGGAAGCTTG
GlnArgGlyP roGlyArgAl aPheValThr IleGlyLysA snLeuArgTh
rArgGluAsp GlnGlyGluH isLeuLeuGl n...GluLys ThrPheGluP
roGluArgTh rArgGluSer IleCysTyrA snArgLysLy sProSerAsn

CCTGCTCGGC TACTACAACC AGTCGGCCGG CGGCACTCAC ACACTGCAGA     250
GGACGAGCCG ATGATGTTGG TCAGCCGGCC GCCGTGAGTG TGTGACGTCT
rLeuLeuGly TyrTyrAsnG lnSerAlaGl yGlyThrHis ThrLeuGlnL
roCysSerAl aThrThrThr SerArgProA laAlaLeuTh rHisCysArg
ProAlaArgL euLeuGlnPr oValGlyArg ArgHisSerH isThrAlaGl
```

Figure 15A.

CMV/RANTES/SAK Sequence

```
         10         20         30         40         50
1234567890 1234567890 1234567890 1234567890 1234567890
           HindIII                XbaI
AGGACGAGCT CTAAGCTTAG ATAAGTAAAA TTCGAGCTCT AGAT            294
TCCTGCTCGA GATTCGAATC TATTCATTTT AAGCTCGAGA TCTA
ysAspGluLe u...Ala... IleSerLysI leArgAlaLe uAsp
ArgThrSerS erLysLeuAr g...ValLys PheGluLeu. ..
uGlyArgAla LeuSerLeuA spLys...As nSerSerSer Arg
```

Figure 15B.

SEQUENCE LISTING

```
<160> NUMBER OF SEQ ID NOS: 25

<210> SEQ ID NO 1
<211> LENGTH: 297
<212> TYPE: DNA
<213> ORGANISM: Artificial Sequence
<220> FEATURE:
<221> NAME/KEY: CDS
<222> LOCATION: (28)...(267)
<223> OTHER INFORMATION: MIP-1beta-SAK

<400> SEQUENCE: 1
gatggtgacc ggagatctgc cgccacc atg ggg gcg atg gct ccg cgc acg ctg      54
                                Met Gly Ala Met Ala Pro Arg Thr Leu
                                 1               5 ctc ctg ctg ctg gcg gcc gcc ctg gcc ccg act cag acc cgc gcg gcg     102
Leu Leu Leu Leu Ala Ala Ala Leu Ala Pro Thr Gln Thr Arg Ala Ala
 10              15                  20                  25 cca atg ggc tct gac cct ccc act tcc ggg ccc gag tat tgg gag cgt     150
Pro Met Gly Ser Asp Pro Pro Thr Ser Gly Pro Glu Tyr Trp Glu Arg
                 30                  35                  40 atc cag aga gga cca ggg aga gca ttt gtt aca ata gga aaa aac ctt     198
Ile Gln Arg Gly Pro Gly Arg Ala Phe Val Thr Ile Gly Lys Asn Leu
             45                  50                  55 cga acc ctg ctc ggc tac tac aac cag tcg gcc ggc ggc act cac aca     246
Arg Thr Leu Leu Gly Tyr Tyr Asn Gln Ser Ala Gly Gly Thr His Thr
         60                  65                  70 ctg cag aag gac gag ctc taa gcttagataa gtaaaattcg agctctagat         297
Leu Gln Lys Asp Glu Leu
     75

<210> SEQ ID NO 2
<211> LENGTH: 79
<212> TYPE: PRT
<213> ORGANISM: Artificial Sequence
<220> FEATURE:
<223> OTHER INFORMATION: MIP-1beta-SAK

<400> SEQUENCE: 2

Met Gly Ala Met Ala Pro Arg Thr Leu Leu Leu Leu Ala Ala Ala
 1               5                  10                  15

Leu Ala Pro Thr Gln Thr Arg Ala Ala Pro Met Gly Ser Asp Pro Pro
                 20                  25                  30

Thr Ser Gly Pro Glu Tyr Trp Glu Arg Ile Gln Arg Gly Pro Gly Arg
             35                  40                  45

Ala Phe Val Thr Ile Gly Lys Asn Leu Arg Thr Leu Leu Gly Tyr Tyr
     50                  55                  60

Asn Gln Ser Ala Gly Gly Thr His Thr Leu Gln Lys Asp Glu Leu
 65                  70                  75
```

```
<210> SEQ ID NO 3
<211> LENGTH: 499
<212> TYPE: DNA
<213> ORGANISM: Artificial Sequence
<220> FEATURE:
<221> NAME/KEY: CDS
<222> LOCATION: (1)...(462)
<223> OTHER INFORMATION: CMV/Mip-1b/p18/OVA/TMYZLL

<400> SEQUENCE: 3 ggt gac cgg aga tct gcc gcc acc atg ggg gcg atg gct ccg cgc acg      48
Gly Asp Arg Arg Ser Ala Ala Thr Met Gly Ala Met Ala Pro Arg Thr
 1               5                  10                  15 ctg ctc ctg ctg ctg gcg gcc gcc ctg gcc ccg act cag acc cgc gcg      96
Leu Leu Leu Leu Leu Ala Ala Ala Leu Ala Pro Thr Gln Thr Arg Ala
            20                  25                  30 gcg cca atg ggc tct gac cct ccc act tcc ggg ccc gag tat tgg gag     144
Ala Pro Met Gly Ser Asp Pro Pro Thr Ser Gly Pro Glu Tyr Trp Glu
        35                  40                  45 cgt atc cag aga gga cca ggg aga gca ttt gtt aca ata ggt aaa acc     192
Arg Ile Gln Arg Gly Pro Gly Arg Ala Phe Val Thr Ile Gly Lys Thr
    50                  55                  60 ggt agc gca gag agc ctg aag ata tct caa gct gtc cat gca gca cat     240
Gly Ser Ala Glu Ser Leu Lys Ile Ser Gln Ala Val His Ala Ala His
 65                 70                  75                  80 gca gaa atc aat gaa gca ggc aga gag gtg ctt aag tgg gag cct cct     288
Ala Glu Ile Asn Glu Ala Gly Arg Glu Val Leu Lys Trp Glu Pro Pro
                85                  90                  95 ccg tcc act gac tct tac atg gtg atc gtt gct gtt ctg ggt gtc ctt     336
Pro Ser Thr Asp Ser Tyr Met Val Ile Val Ala Val Leu Gly Val Leu
            100                 105                 110 gga gct atg gcc atc att gga gct gtg gtg gct ttt gtg atg aag aga     384
Gly Ala Met Ala Ile Ile Gly Ala Val Val Ala Phe Val Met Lys Arg
        115                 120                 125 agg aga gct agc cac gcc ggc tat cag acc ata gtg tcc ttc cat gat     432
Arg Arg Ala Ser His Ala Gly Tyr Gln Thr Ile Val Ser Phe His Asp
    130                 135                 140 gac agc gac gaa gac ctc tta cac ata tag ataaccactg cagtggatcg      482
Asp Ser Asp Glu Asp Leu Leu His Ile
145                 150 ggtgaccatc gccgcgg                                                  499

<210> SEQ ID NO 4
<211> LENGTH: 153
<212> TYPE: PRT
<213> ORGANISM: Artificial Sequence
<220> FEATURE:
<223> OTHER INFORMATION: CMV/Mip-1b/p18/OVA/TMYZLL

<400> SEQUENCE: 4

Gly Asp Arg Arg Ser Ala Ala Thr Met Gly Ala Met Ala Pro Arg Thr
 1               5                  10                  15

Leu Leu Leu Leu Leu Ala Ala Ala Leu Ala Pro Thr Gln Thr Arg Ala
            20                  25                  30

Ala Pro Met Gly Ser Asp Pro Pro Thr Ser Gly Pro Glu Tyr Trp Glu
        35                  40                  45

Arg Ile Gln Arg Gly Pro Gly Arg Ala Phe Val Thr Ile Gly Lys Thr
    50                  55                  60

Gly Ser Ala Glu Ser Leu Lys Ile Ser Gln Ala Val His Ala Ala His
 65                 70                  75                  80
```

```
Ala Glu Ile Asn Glu Ala Gly Arg Glu Val Leu Lys Trp Glu Pro Pro
                85                  90                  95

Pro Ser Thr Asp Ser Tyr Met Val Ile Val Ala Val Leu Gly Val Leu
            100                 105                 110

Gly Ala Met Ala Ile Ile Gly Ala Val Val Ala Phe Val Met Lys Arg
        115                 120                 125

Arg Arg Ala Ser His Ala Gly Tyr Gln Thr Ile Val Ser Phe His Asp
    130                 135                 140

Asp Ser Asp Glu Asp Leu Leu His Ile
145                 150

<210> SEQ ID NO 5
<211> LENGTH: 490
<212> TYPE: DNA
<213> ORGANISM: Artificial Sequence
<220> FEATURE:
<221> NAME/KEY: CDS
<222> LOCATION: (1)...(453)
<223> OTHER INFORMATION: CMV/Mip-3b/p18/OVA/TMYZLL

<400> SEQUENCE: 5 ggt gac cgg aga tct gcc gcc acc atg ggg gcg atg gct ccg cgc acg     48
Gly Asp Arg Arg Ser Ala Ala Thr Met Gly Ala Met Ala Pro Arg Thr
1               5                   10                  15 ctg ctc ctg ctg ctg gcg gcc gcc ctg gcc ccg act cag acc cgc gcg     96
Leu Leu Leu Leu Leu Ala Ala Ala Leu Ala Pro Thr Gln Thr Arg Ala
                20                  25                  30 ggt gct aat gat gcg gaa gac ggg ccc gag tat tgg gag cgt atc cag    144
Gly Ala Asn Asp Ala Glu Asp Gly Pro Glu Tyr Trp Glu Arg Ile Gln
            35                  40                  45 aga gga cca ggg aga gca ttt gtt aca ata ggt aaa acc ggt agc gca    192
Arg Gly Pro Gly Arg Ala Phe Val Thr Ile Gly Lys Thr Gly Ser Ala
        50                  55                  60 gag agc ctg aag ata tct caa gct gtc cat gca gca cat gca gaa atc    240
Glu Ser Leu Lys Ile Ser Gln Ala Val His Ala Ala His Ala Glu Ile
65                  70                  75                  80 aat gaa gca ggc aga gag gtg ctt aag tgg gag cct cct ccg tcc act    288
Asn Glu Ala Gly Arg Glu Val Leu Lys Trp Glu Pro Pro Pro Ser Thr
                85                  90                  95 gac tct tac atg gtg atc gtt gct gtt ctg ggt gtc ctt gga gct atg    336
Asp Ser Tyr Met Val Ile Val Ala Val Leu Gly Val Leu Gly Ala Met
            100                 105                 110 gcc atc att gga gct gtg gtg gct ttt gtg atg aag aga agg aga gct    384
Ala Ile Ile Gly Ala Val Val Ala Phe Val Met Lys Arg Arg Arg Ala
        115                 120                 125 agc cac gcc ggc tat cag acc ata gtg tcc ttc cat gat gac agc gac    432
Ser His Ala Gly Tyr Gln Thr Ile Val Ser Phe His Asp Asp Ser Asp
    130                 135                 140 gaa gac ctc tta cac ata tag ataaccactg cagtggatcg ggtgaccatc       483
Glu Asp Leu Leu His Ile
145                 150 gccgcgg                                                            490

<210> SEQ ID NO 6
<211> LENGTH: 150
<212> TYPE: PRT
<213> ORGANISM: Artificial Sequence
<220> FEATURE:
<223> OTHER INFORMATION: CMV/Mip-3b/p18/OVA/TMYZLL

<400> SEQUENCE: 6
```

```
Gly Asp Arg Arg Ser Ala Ala Thr Met Gly Ala Met Ala Pro Arg Thr
 1               5                  10                  15

Leu Leu Leu Leu Leu Ala Ala Ala Leu Ala Pro Thr Gln Thr Arg Ala
                20                  25                  30

Gly Ala Asn Asp Ala Glu Asp Gly Pro Glu Tyr Trp Glu Arg Ile Gln
            35                  40                  45

Arg Gly Pro Gly Arg Ala Phe Val Thr Ile Gly Lys Thr Gly Ser Ala
        50                  55                  60

Glu Ser Leu Lys Ile Ser Gln Ala Val His Ala Ala His Ala Glu Ile
65                  70                  75                  80

Asn Glu Ala Gly Arg Glu Val Leu Lys Trp Glu Pro Pro Ser Thr
                85                  90                  95

Asp Ser Tyr Met Val Ile Val Ala Val Leu Gly Val Leu Gly Ala Met
            100                 105                 110

Ala Ile Ile Gly Ala Val Val Ala Phe Val Met Lys Arg Arg Arg Ala
            115                 120                 125

Ser His Ala Gly Tyr Gln Thr Ile Val Ser Phe His Asp Asp Ser Asp
        130                 135                 140

Glu Asp Leu Leu His Ile
145             150

<210> SEQ ID NO 7
<211> LENGTH: 496
<212> TYPE: DNA
<213> ORGANISM: Artificial Sequence
<220> FEATURE:
<221> NAME/KEY: CDS
<222> LOCATION: (1)...(459)
<223> OTHER INFORMATION: CMV/TCA-3/p18/OVA/TMYZLL

<400> SEQUENCE: 7 ggt gac cgg aga tct gcc gcc acc atg ggg gcg atg gct ccg cgc acg      48
Gly Asp Arg Arg Ser Ala Ala Thr Met Gly Ala Met Ala Pro Arg Thr
 1               5                  10                  15 ctg ctc ctg ctg ctg gcg gcc gcc ctg gcc ccg act cag acc cgc gcg      96
Leu Leu Leu Leu Leu Ala Ala Ala Leu Ala Pro Thr Gln Thr Arg Ala
                20                  25                  30 aag agc atg ctt acg gtc tcc aat agc ggg ccc gag tat tgg gag cgt     144
Lys Ser Met Leu Thr Val Ser Asn Ser Gly Pro Glu Tyr Trp Glu Arg
            35                  40                  45 atc cag aga gga cca ggg aga gca ttt gtt aca ata ggt aaa acc ggt     192
Ile Gln Arg Gly Pro Gly Arg Ala Phe Val Thr Ile Gly Lys Thr Gly
        50                  55                  60 agc gca gag agc ctg aag ata tct caa gct gtc cat gca gca cat gca     240
Ser Ala Glu Ser Leu Lys Ile Ser Gln Ala Val His Ala Ala His Ala
65                  70                  75                  80 gaa atc aat gaa gca ggc aga gag gtg ctt aag tgg gag cct cct ccg     288
Glu Ile Asn Glu Ala Gly Arg Glu Val Leu Lys Trp Glu Pro Pro Pro
                85                  90                  95 tcc act gac tct tac atg gtg atc gtt gct gtt ctg ggt gtc ctt gga     336
Ser Thr Asp Ser Tyr Met Val Ile Val Ala Val Leu Gly Val Leu Gly
            100                 105                 110 gct atg gcc atc att gga gct gtg gtg gct ttt gtg atg aag aga agg     384
Ala Met Ala Ile Ile Gly Ala Val Val Ala Phe Val Met Lys Arg Arg
            115                 120                 125 aga gct agc cac gcc ggc tat cag acc ata gtg tcc ttc cat gat gac     432
Arg Ala Ser His Ala Gly Tyr Gln Thr Ile Val Ser Phe His Asp Asp
        130                 135                 140 agc gac gaa gac ctc tta cac ata tag ataaccactg cagtggatcg           479
Ser Asp Glu Asp Leu Leu His Ile
145             150
```

```
Ser Asp Glu Asp Leu Leu His Ile
145                 150 ggtgaccatc gccgcgg                                                        496

<210> SEQ ID NO 8
<211> LENGTH: 152
<212> TYPE: PRT
<213> ORGANISM: Artificial Sequence
<220> FEATURE:
<223> OTHER INFORMATION: CMV/TCA-3/P18/OVA/TMYZLL

<400> SEQUENCE: 8

Gly Asp Arg Arg Ser Ala Ala Thr Met Gly Ala Met Ala Pro Arg Thr
 1               5                  10                  15

Leu Leu Leu Leu Leu Ala Ala Ala Leu Ala Pro Thr Gln Thr Arg Ala
             20                  25                  30

Lys Ser Met Leu Thr Val Ser Asn Ser Gly Pro Glu Tyr Trp Glu Arg
         35                  40                  45

Ile Gln Arg Gly Pro Gly Arg Ala Phe Val Thr Ile Gly Lys Thr Gly
     50                  55                  60

Ser Ala Glu Ser Leu Lys Ile Ser Gln Ala Val His Ala Ala His Ala
 65                  70                  75                  80

Glu Ile Asn Glu Ala Gly Arg Glu Val Leu Lys Trp Glu Pro Pro Pro
                 85                  90                  95

Ser Thr Asp Ser Tyr Met Val Ile Val Ala Val Leu Gly Val Leu Gly
            100                 105                 110

Ala Met Ala Ile Ile Gly Ala Val Val Ala Phe Val Met Lys Arg Arg
        115                 120                 125

Arg Ala Ser His Ala Gly Tyr Gln Thr Ile Val Ser Phe His Asp Asp
    130                 135                 140

Ser Asp Glu Asp Leu Leu His Ile
145                 150

<210> SEQ ID NO 9
<211> LENGTH: 493
<212> TYPE: DNA
<213> ORGANISM: Artificial Sequence
<220> FEATURE:
<221> NAME/KEY: CDS
<222> LOCATION: (1)...(456)
<223> OTHER INFORMATION: CMV/SDF-1/p18/OVA/TMYZLL

<400> SEQUENCE: 9 ggt gac cgg aga tct gcc gcc acc atg ggg gcg atg gct ccg cgc acg        48
Gly Asp Arg Arg Ser Ala Ala Thr Met Gly Ala Met Ala Pro Arg Thr
 1               5                  10                  15 ctg ctc ctg ctg ctg gcg gcc gcc ctg gcc ccg act cag acc cgc gcg        96
Leu Leu Leu Leu Leu Ala Ala Ala Leu Ala Pro Thr Gln Thr Arg Ala
             20                  25                  30 aaa cca gtc agc ctg agc tac cga ggg ccc gag tat tgg gag cgt atc       144
Lys Pro Val Ser Leu Ser Tyr Arg Gly Pro Glu Tyr Trp Glu Arg Ile
         35                  40                  45 cag aga gga cca ggg aga gca ttt gtt aca ata ggt aaa acc ggt agc       192
Gln Arg Gly Pro Gly Arg Ala Phe Val Thr Ile Gly Lys Thr Gly Ser
     50                  55                  60 gca gag agc ctg aag ata tct caa gct gtc cat gca gca cat gca gaa       240
Ala Glu Ser Leu Lys Ile Ser Gln Ala Val His Ala Ala His Ala Glu
 65                  70                  75                  80 atc aat gaa gca ggc aga gag gtg ctt aag tgg gag cct cct ccg tcc       288
Ile Asn Glu Ala Gly Arg Glu Val Leu Lys Trp Glu Pro Pro Pro Ser
```

-continued

```
                       85                  90                  95
act gac tct tac atg gtg atc gtt gct gtt ctg ggt gtc ctt gga gct        336
Thr Asp Ser Tyr Met Val Ile Val Ala Val Leu Gly Val Leu Gly Ala
                100                 105                 110 atg gcc atc att gga gct gtg gtg gct ttt gtg atg aag aga agg aga        384
Met Ala Ile Ile Gly Ala Val Val Ala Phe Val Met Lys Arg Arg Arg
            115                 120                 125 gct agc cac gcc ggc tat cag acc ata gtg tcc ttc cat gat gac agc        432
Ala Ser His Ala Gly Tyr Gln Thr Ile Val Ser Phe His Asp Asp Ser
        130                 135                 140 gac gaa gac ctc tta cac ata tag ataaccactg cagtggatcg ggtgaccatc       486
Asp Glu Asp Leu Leu His Ile
145             150 gccgcgg                                                                493
```

<210> SEQ ID NO 10
<211> LENGTH: 151
<212> TYPE: PRT
<213> ORGANISM: Artificial Sequence
<220> FEATURE:
<223> OTHER INFORMATION: CMV/SDF-1/p18/OVA/TMYZLL

<400> SEQUENCE: 10

```
Gly Asp Arg Arg Ser Ala Ala Thr Met Gly Ala Met Ala Pro Arg Thr
1               5                   10                  15

Leu Leu Leu Leu Leu Ala Ala Ala Leu Ala Pro Thr Gln Thr Arg Ala
            20                  25                  30

Lys Pro Val Ser Leu Ser Tyr Arg Gly Pro Glu Tyr Trp Glu Arg Ile
        35                  40                  45

Gln Arg Gly Pro Gly Arg Ala Phe Val Thr Ile Gly Lys Thr Gly Ser
    50                  55                  60

Ala Glu Ser Leu Lys Ile Ser Gln Ala Val His Ala Ala His Ala Glu
65                  70                  75                  80

Ile Asn Glu Ala Gly Arg Glu Val Leu Lys Trp Glu Pro Pro Pro Ser
                85                  90                  95

Thr Asp Ser Tyr Met Val Ile Val Ala Val Leu Gly Val Leu Gly Ala
            100                 105                 110

Met Ala Ile Ile Gly Ala Val Val Ala Phe Val Met Lys Arg Arg Arg
        115                 120                 125

Ala Ser His Ala Gly Tyr Gln Thr Ile Val Ser Phe His Asp Asp Ser
    130                 135                 140

Asp Glu Asp Leu Leu His Ile
145             150
```

<210> SEQ ID NO 11
<211> LENGTH: 291
<212> TYPE: DNA
<213> ORGANISM: Artificial Sequence
<220> FEATURE:
<221> NAME/KEY: CDS
<222> LOCATION: (1)...(261)
<223> OTHER INFORMATION: CMV/Crg-2/SAK

<400> SEQUENCE: 11

```
gat ggt gac cgg aga tct gcc gcc acc atg ggg gcg atg gct ccg cgc        48
Asp Gly Asp Arg Arg Ser Ala Ala Thr Met Gly Ala Met Ala Pro Arg
1               5                   10                  15 acg ctg ctc ctg ctg ctg gcg gcc gcc ctg gcc ccg act cag acc cgc        96
Thr Leu Leu Leu Leu Leu Ala Ala Ala Leu Ala Pro Thr Gln Thr Arg
            20                  25                  30
```

-continued

```
gcg atc cct ctc gca agg acg gtc aga ggg ccc gag tat tgg gag cgt    144
Ala Ile Pro Leu Ala Arg Thr Val Arg Gly Pro Glu Tyr Trp Glu Arg
         35                  40                  45 atc cag aga gga cca ggg aga gca ttt gtt aca ata gga aaa aac ctt    192
Ile Gln Arg Gly Pro Gly Arg Ala Phe Val Thr Ile Gly Lys Asn Leu
 50                  55                  60 cga acc ctg ctc ggc tac tac aac cag tcg gcc ggc ggc act cac aca    240
Arg Thr Leu Leu Gly Tyr Tyr Asn Gln Ser Ala Gly Gly Thr His Thr
 65                  70                  75                  80 ctg cag aag gac gag ctc taa gcttagataa gtaaaattcg agctctagat       291
Leu Gln Lys Asp Glu Leu
                 85

<210> SEQ ID NO 12
<211> LENGTH: 86
<212> TYPE: PRT
<213> ORGANISM: Artificial Sequence
<220> FEATURE:
<223> OTHER INFORMATION: CMV/Crg-2/SAK

<400> SEQUENCE: 12

Asp Gly Asp Arg Arg Ser Ala Ala Thr Met Gly Ala Met Ala Pro Arg
 1               5                  10                  15

Thr Leu Leu Leu Leu Ala Ala Ala Leu Ala Pro Thr Gln Thr Arg
             20                  25                  30

Ala Ile Pro Leu Ala Arg Thr Val Arg Gly Pro Glu Tyr Trp Glu Arg
         35                  40                  45

Ile Gln Arg Gly Pro Gly Arg Ala Phe Val Thr Ile Gly Lys Asn Leu
 50                  55                  60

Arg Thr Leu Leu Gly Tyr Tyr Asn Gln Ser Ala Gly Gly Thr His Thr
 65                  70                  75                  80

Leu Gln Lys Asp Glu Leu
                 85

<210> SEQ ID NO 13
<211> LENGTH: 294
<212> TYPE: DNA
<213> ORGANISM: Artificial Sequence
<220> FEATURE:
<221> NAME/KEY: CDS
<222> LOCATION: (1)...(264)
<223> OTHER INFORMATION: CMV/RANTES/SAK

<400> SEQUENCE: 13 gat ggt gac cgg aga tct gcc gcc acc atg ggg gcg atg gct ccg cgc    48
Asp Gly Asp Arg Arg Ser Ala Ala Thr Met Gly Ala Met Ala Pro Arg
 1               5                  10                  15 acg ctg ctc ctg ctg ctg gcg gcc gcc ctg gcc ccg act cag acc cgc    96
Thr Leu Leu Leu Leu Leu Ala Ala Ala Leu Ala Pro Thr Gln Thr Arg
             20                  25                  30 gcg tca cca tat ggc tcg gac acc act ccc ggg ccc gag tat tgg gag    144
Ala Ser Pro Tyr Gly Ser Asp Thr Thr Pro Gly Pro Glu Tyr Trp Glu
         35                  40                  45 cgt atc cag aga gga cca ggg aga gca ttt gtt aca ata gga aaa aac    192
Arg Ile Gln Arg Gly Pro Gly Arg Ala Phe Val Thr Ile Gly Lys Asn
 50                  55                  60 ctt cga acc ctg ctc ggc tac tac aac cag tcg gcc ggc ggc act cac    240
Leu Arg Thr Leu Leu Gly Tyr Tyr Asn Gln Ser Ala Gly Gly Thr His
 65                  70                  75                  80 aca ctg cag aag gac gag ctc taa gcttagataa gtaaaattcg agctctagat   294
Thr Leu Gln Lys Asp Glu Leu
```

-continued

```
<210> SEQ ID NO 14
<211> LENGTH: 87
<212> TYPE: PRT
<213> ORGANISM: Artificial Sequence
<220> FEATURE:
<223> OTHER INFORMATION: CMV/RANTES/SAK

<400> SEQUENCE: 14

Asp Gly Asp Arg Arg Ser Ala Ala Thr Met Gly Ala Met Ala Pro Arg
1               5                   10                  15

Thr Leu Leu Leu Leu Leu Ala Ala Leu Ala Pro Thr Gln Thr Arg
            20                  25                  30

Ala Ser Pro Tyr Gly Ser Asp Thr Thr Pro Gly Pro Glu Tyr Trp Glu
                35                  40                  45

Arg Ile Gln Arg Gly Pro Gly Arg Ala Phe Val Thr Ile Gly Lys Asn
            50                  55                  60

Leu Arg Thr Leu Leu Gly Tyr Tyr Asn Gln Ser Ala Gly Gly Thr His
65                  70                  75                  80

Thr Leu Gln Lys Asp Glu Leu
                85

<210> SEQ ID NO 15
<211> LENGTH: 10
<212> TYPE: PRT
<213> ORGANISM: Mus musculus

<400> SEQUENCE: 15

Gln Pro Asp Ala Val Asn Ala Pro Leu Thr
1               5                   10

<210> SEQ ID NO 16
<211> LENGTH: 9
<212> TYPE: PRT
<213> ORGANISM: Mus musculus

<400> SEQUENCE: 16

Lys Ser Met Leu Thr Val Ser Asn Ser
1               5

<210> SEQ ID NO 17
<211> LENGTH: 8
<212> TYPE: PRT
<213> ORGANISM: Mus musculus

<400> SEQUENCE: 17

Ile Pro Leu Ala Arg Thr Val Arg
1               5

<210> SEQ ID NO 18
<211> LENGTH: 8
<212> TYPE: PRT
<213> ORGANISM: Mus musculus

<400> SEQUENCE: 18

Lys Pro Val Ser Leu Ser Tyr Arg
1               5

<210> SEQ ID NO 19
<211> LENGTH: 7
<212> TYPE: PRT
<213> ORGANISM: Mus musculus
```

-continued

```
<400> SEQUENCE: 19

Gly Ala Asn Asp Ala Glu Asp
1               5

<210> SEQ ID NO 20
<211> LENGTH: 10
<212> TYPE: PRT
<213> ORGANISM: Mus musculus

<400> SEQUENCE: 20

Ala Pro Tyr Gly Ala Asp Thr Pro Thr Ala
1               5                   10

<210> SEQ ID NO 21
<211> LENGTH: 9
<212> TYPE: PRT
<213> ORGANISM: Mus musculus

<400> SEQUENCE: 21

Ser Pro Tyr Gly Ser Asp Thr Thr Pro
1               5

<210> SEQ ID NO 22
<211> LENGTH: 10
<212> TYPE: PRT
<213> ORGANISM: Mus musculus

<400> SEQUENCE: 22

Ala Pro Met Gly Ser Asp Pro Pro Thr Ser
1               5                   10

<210> SEQ ID NO 23
<211> LENGTH: 4
<212> TYPE: PRT
<213> ORGANISM: Artificial Sequence
<220> FEATURE:
<223> OTHER INFORMATION: Endoplasmic reticulum import signal sequence

<400> SEQUENCE: 23

Lys Asp Glu Leu
1

<210> SEQ ID NO 24
<211> LENGTH: 10
<212> TYPE: PRT
<213> ORGANISM: Human immunodeficiency virus (HIV)
<220> FEATURE:
<223> OTHER INFORMATION: Residues 318-327 of gp120 (GenBank accession
      number gi224364)

<400> SEQUENCE: 24

Arg Gly Pro Gly Arg Ala Phe Val Thr Ile
1               5                   10

<210> SEQ ID NO 25
<211> LENGTH: 9
<212> TYPE: PRT
<213> ORGANISM: Artificial Sequence
<220> FEATURE:
<223> OTHER INFORMATION: Control peptide

<400> SEQUENCE: 25

Lys Gly Pro Asp Lys Gly Asn Glu Phe
1               5
```

USE OF IMMUNOPOTENTIATING SEQUENCES FOR INDUCING IMMUNE RESPONSE

RELATED APPLICATIONS

This application claims priority to the U.S. provisional application serial No. 60/106,506, filed on Oct. 30, 1998.

FIELD OF THE INVENTION

This invention relates to a composition and method for inducing an immune response. In particular, the invention relates to nucleic acid expression vectors encoding immunopotentiating chemokines as well as immunogenic polypeptides. The invention also relates to methods of manufacturing various immunogenic compositions, and methods of using such compositions to treat cancer and infectious disease.

BACKGROUND OF THE INVENTION

The immune system protects individuals against disease and infection by viruses, bacteria or other infectious agents. The immune system is able to recognize cells of different individuals, including different allogeneic hosts. Ideally, the immune system functions to eliminate an infectious agent from a mammalian host. Specific immune mechanisms are involved in presenting infection with foreign agents, in resolution of such infections, and in control of cancer cells. Resolution of most virus infections (as well as infection with many other intracellular agents) and elimination of cancer cells is the result of a successful cellular (e.g., $T_h1$ helper T cell and cytotoxic T cell) immune response. The cellular immune response results from activation of certain lymphocytes known as T cells.

Many traditional vaccines expose the immune system to a foreign antigen such as an antigen of an infectious agent to elicit an antigen-specific immune response. The immune response is often predominantly humoral, in which the presence of a foreign antigen elicits the production of antibodies specific for the antigen. For example, an infectious agent antigen may elicit the production of antibodies which neutralize the infectivity of the infectious agent or toxin produced by the agent. Examples include polio and hepatitis A and B, measles, Varicella-zoster, parvovirus and rabies virus antigens. Toxic antigens produced by infectious agents include tetanus toxin, botulinum toxin, diphtheria toxin and pertussis toxin. (See Fundamental Virology, Fields et al. eds., 3rd ed., Lippincott-Raven, New York 1996; and Microbiology, Davis et al. eds., 4th ed., Lippincott, New York, 1990). This is in contrast to a cellular response, e.g. by activated T cells.

Recently, vaccination using DNA fragments has emerged as a viable method for inducing an immune response in animal hosts. DNA vaccination has enormous potential to revolutionize human health by obliterating many infectious diseases, not only in the industrialized nations but also in the Third World. There have been intense efforts to develop vaccines that induce a protective response based on induction of antibodies or cellular responses. Recent studies have shown that DNA vaccination involving the direct injection into animals of genes encoding viral proteins (subunit vaccines), rather than attenuated or killed viruses, can evoke a protective effect against challenge with whole virus from which the gene was derived [Donnelly, J. J. et al.; *Annu. Rev. Immunol.* 15:617–648 (1997)].

Thus, direct injection into animals of a DNA expression vector, encoding a potentially pathogenic protein, has demonstrated that a protective specific immune response, both humoral and cellular, can be elicited to that protein product. It is thought that bone-marrow-derived, antigen-presenting cells (APCs) take up the DNA plasmid and express the encoded gene product in the lymph nodes—the tissue in which an immune response is orchestrated. This ultimately results in the generation of specific antibodies and cytotoxic T lymphocytes.

The use of subunit vaccines suffers from at least two limitations, namely, (i) the presence of certain viral proteins, e.g., HIV gp160, can themselves have deleterious effects even in the absence of infectious virus (Mellado, M., et al.; *Vaccine* 15:1111–1115 (1998)) and (ii) expression vectors can only be constructed to contain a limited number of genes (10–15 kb). Thus, a DNA vaccine which presents several viral proteins for recognition by the immune response must comprise a mixture of plasmids each containing 1–3 genes, which limits the amount of each vector species that can be administered.

As a consequence, there is a need to minimize the size of sequences necessary to elicit a protective immune response. The minimization of sequence size will allow the use of small vectors, which enter cells more efficiently than larger vectors, and obviate the potentially harmful effects associated with expression of whole viral proteins.

SUMMARY OF THE INVENTION

The present invention features a novel DNA expression vector for inducing an immune response in a mammalian host that includes at least one sequence encoding an immunogenic polypeptide and at least one sequence encoding an immunopotentiating chemokine capable of boosting the host's immune response to the immunogenic polypeptide. The chemokines of the invention are preferably selected according to the animal to be treated, e.g., murine chemokines if the animal is a mouse or human chemokines for human beings.

In another aspect of the invention, the DNA expression vector is combined with a suitable carrier to yield a pharmaceutical composition that would be effective in inducing an immune response in the host.

The invention also relates to a method of inducing an immune response in a mammalian host by administering an effective amount of the pharmaceutical composition. The immune response may be in the form of a protective challenge or a therapeutic effect.

Additionally, the invention features a method for manufacturing pharmaceutical compositions comprising the step of combining the DNA expression vector of the invention with an acceptable carrier.

BRIEF DESCRIPTION OF THE FIGURES

FIG. 1A is a schematic diagram of a plasmid based on the SAK construct (not to scale) showing positions of epitopes and targeting motifs without the MIP-1β sequence.

FIG. 1B is a schematic diagram of a plasmid based on the SAK construct (not to scale) showing positions of epitopes and targeting motifs with the MIP-1β sequence.

FIG. 3 also shows the specific lysis results using a control peptide, the Dd-binding MPI peptide, for the aforementioned three vectors.

FIG. 9A is a schematic diagram of a plasmid based on the SAK construct (not to scale) showing positions of epitopes and targeting motifs without the MIP-1β sequence.

FIG. 9B is a schematic diagram of a plasmid based on the SAK construct (not to scale) showing positions of epitopes and targeting motifs with the MIP-1β sequence.

FIGS. 10A and 10B provide the amino acid (SEQ ID NO:4) and nucleotide sequence (SEQ ID NO:3) for the MIP-1β-SAO-YZLL construct.

FIGS. 11A and 11B provide the amino acid (SEQ ID NO:6) and nucleotide sequence (SEQ ID NO:5) for the MIP-3β-SAO-YZLL construct.

FIGS. 12A and 12B provide the amino acid (SEQ ID NO:8) and nucleotide sequence (SEQ ID NO:7) for the SDF-1-SAO-YZLL construct.

FIGS. 13A and 13B provide the amino acid (SEQ ID NO:10) and nucleotide sequence (SEQ ID NO:9) for the TCA-3-SAO-YZLL construct.

FIGS. 14A and 14B provide the amino acid (SEQ ID NO:12) and nucleotide sequence (SEQ ID NO:11) for the Crg-2-SAK construct.

FIGS. 15A and 15B provide the amino acid (SEQ ID NO:14) and nucleotide sequence (SEQ ID NO:13) for the RANTES-SAK construct.

DESCRIPTION OF THE INVENTION

Figure 2:
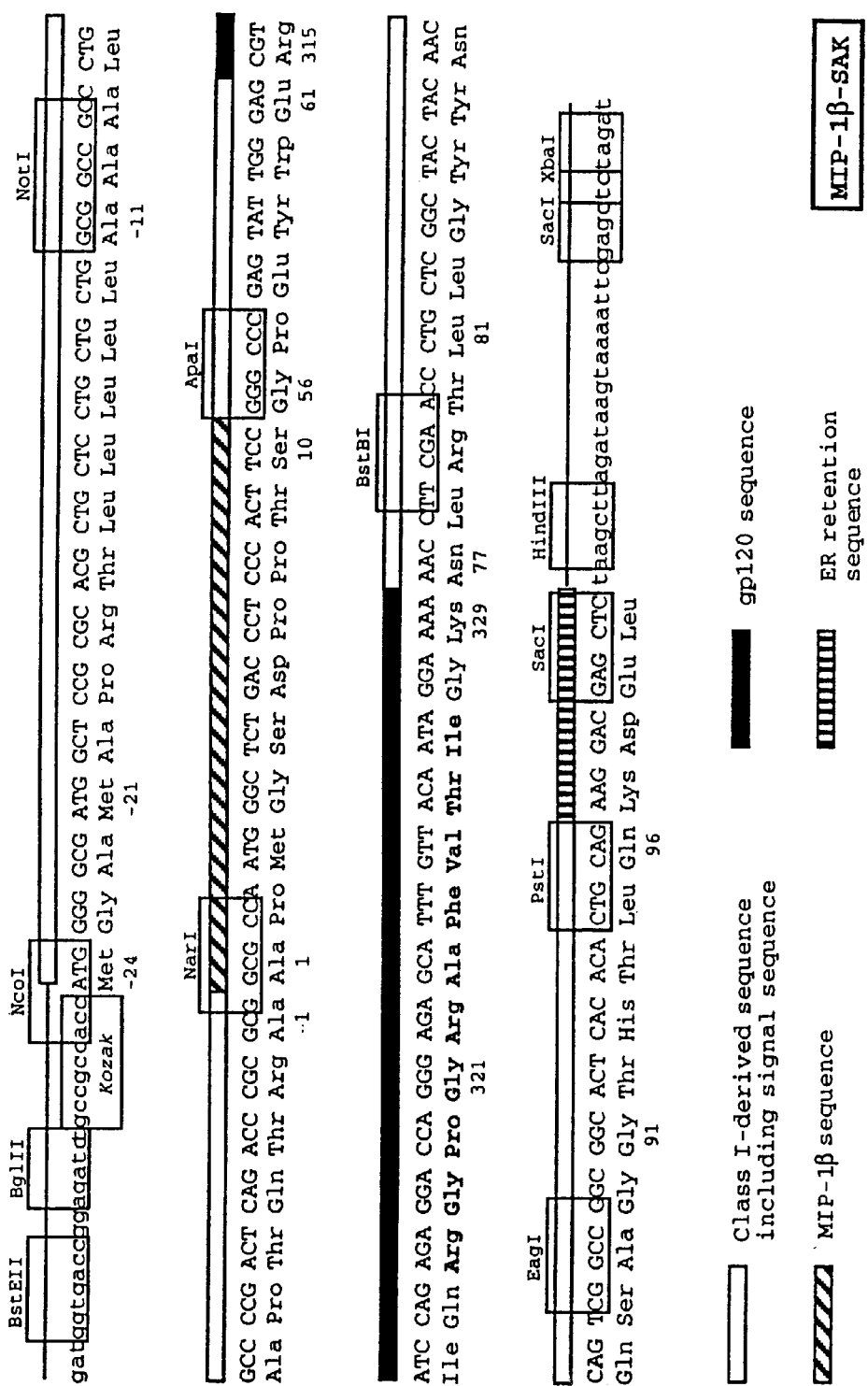
FIG. 2 is the amino acid (SEQ ID NO:2) and nucleotide sequence (SEQ ID NO:1) of the MIP-1β-SAK construct.
Figure 3:
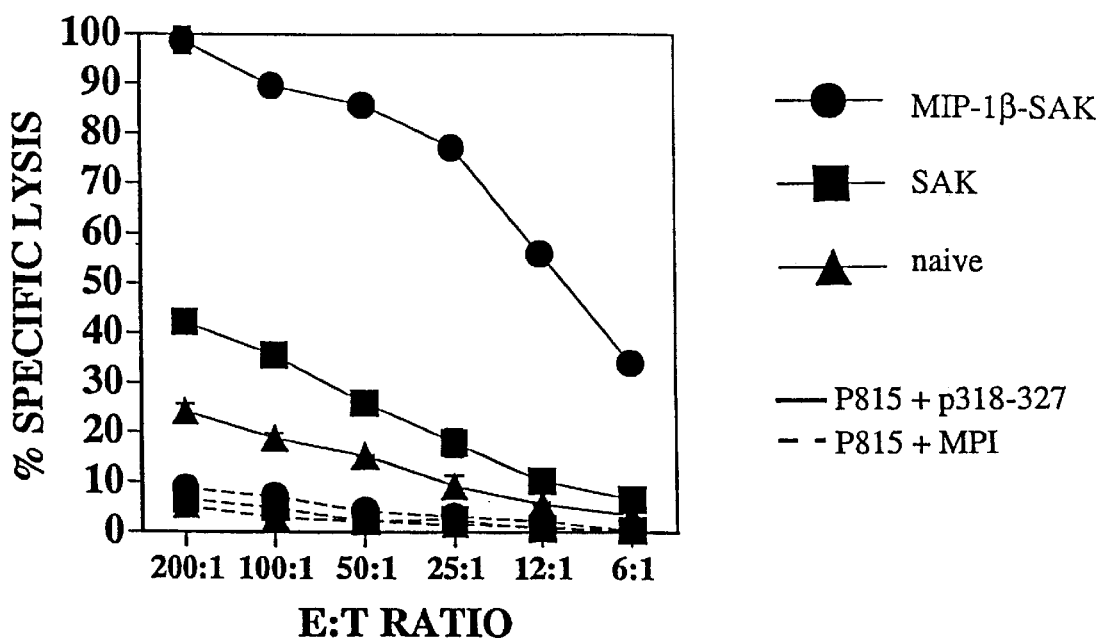
FIG. 3 is a plot of representative $^{51}$Cr-release assay using spleen cells from dm2 mice which were injected and boosted with the SAK construct, with and without the MIP-1β sequence, as well as a naive vector. The figure compares the percentage specific lysis as a measure of immune response to the HIV gp120 coat protein for the SAK construct with and without the MIP-1β sequence, as well as a naive vector.
Figure 4:
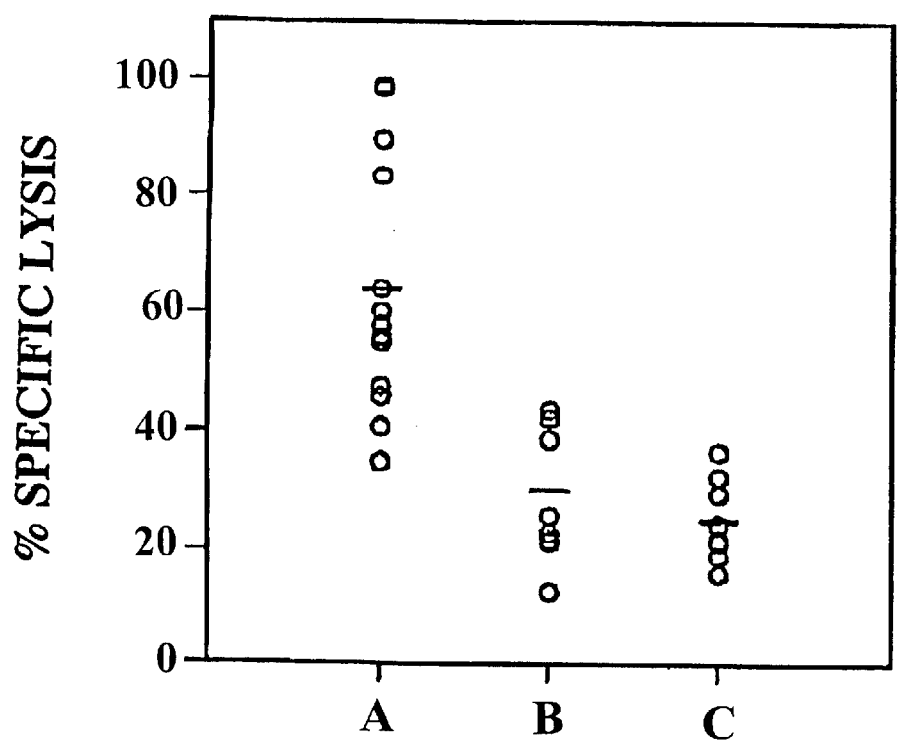
FIG. 4 is a summary plot of maximum specific lysis by cytotoxic T lymphocytes in a Dm2 mice injected with MIP-1β-SAK (A), SAK (B) and naive control (C).
Figure 5:
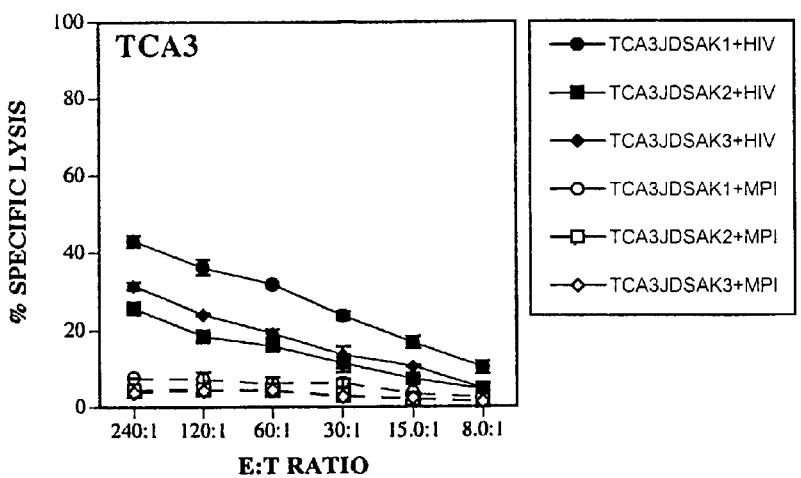
FIG. 5, FIG. 6 and FIG. 7 are plots of representative $^{51}$Cr-release assay using spleen cells from three separate dm2 mice which were injected and boosted with the JDSAK construct, with the TCA-3 sequence, the SDF-1 sequence, and without an immunopotentiating sequence, respectively, as well as a naive vector.
Figure 6:
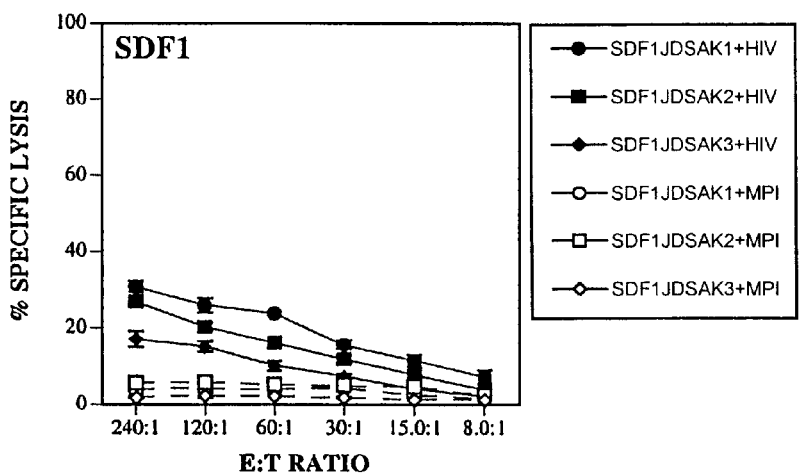
Figure 7:
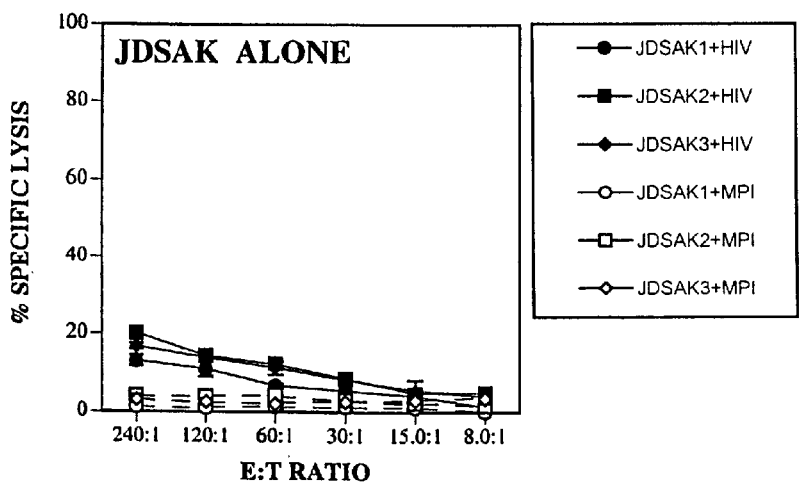
Figure 8:
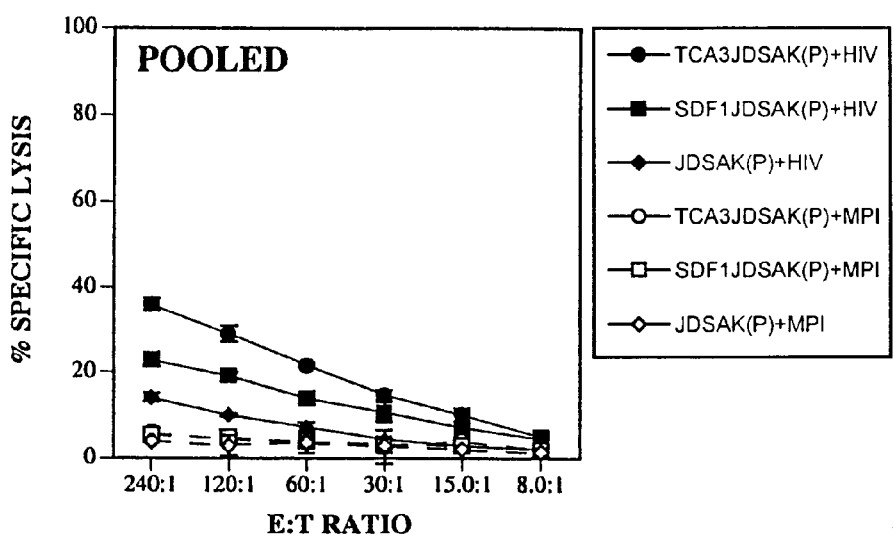
FIG. 8 is a plot of representative $^{51}$Cr-release assay using spleen cells from female mice which were injected twice with the JDSAK construct, with the TCA-3 sequence, the SDF-1 sequence, and without an immunopotentiating sequence. The figures compare the percentage specific lysis as a measure of immune response to the HIV gp120 coat protein for the JDSAK construct with the TCA-3 sequence, the SDF-1 sequence and without any immunopotentiating sequence. The figure also shows the specific lysis results using a control peptide, the Dd-binding MPI peptide, for the aforementioned three vectors.

It is to be understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include the plural reference stated otherwise. Thus, for example, reference to "a host cell" includes a plurality of such host cells, reference to the "DNA expression vector" is a reference to one or more DNA expression vectors and equivalents thereof known to those skilled in the art, and so forth.

Unless defined otherwise, all technical and scientific terms used herein have the same meanings as commonly understood by one of ordinary skill in the art to which this invention belongs. Although methods and materials similar or equivalent to those described herein can be used in the practice or testing of the present invention, the preferred methods, devices, and materials are now described. All publications cited herein are incorporated hereby by reference in their entirety for the purpose of describing and disclosing the cell lines, vectors, and methodologies which are reported in the publications which might be used in connection with the invention. Nothing herein is to be construed as an admission that the invention is not entitled to antedate such disclosure.

"Nucleic acid sequence," and like terms, such as "gene" or "mini-gene" as used herein refer to an oligonucleotide, nucleotide, or polynucleotide, and fragments or portions thereof, and to DNA or RNA of genomic or synthetic origin which may be single- or double-stranded, and represent the sense or antisense strand.

"Polypeptide" is recited herein to refer to an amino acid sequence of a naturally occurring protein molecule, and like terms, such as "amino acid sequence" or "protein" are not meant to limit the amino acid sequence to the complete, native amino acid sequence associated with the recited protein molecule. Use of the term "polypeptide" is meant to include variants of said amino acid sequence.

A "variant" of a polypeptide, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively. "Immunogenic polypeptides" to be expressed by the DNA expression vectors of the invention consist of one or more selected antigens or epitopes of an infectious agent or cancer, or of a transplantation antigen, allergen or autoantigen. The term "immunogenic polypeptide" is used interchangeably with like terms, such as, "antigenic peptide," "antigenic polypeptide," "epitope," "epitope peptide," "antigen," etc.

THE INVENTION

The mammalian immune system includes B cells and different classes of T cells. CD8+T (commonly cytotoxic T) cells recognize antigen peptide plus MHC class I complex. Appropriate T cell activation can result in antigen-specific cytotoxic T lymphocytes (CTLs) able to kill target cells expressing the specific viral or cancer antigens. The invention is directed to boosting CTL production, during an immune response, by use of immunopotentiating chemokines or fragments thereof The increase in CTL production is significant enough that even fragments of immunogenic polypeptides yield a satisfactory immune response, thereby allowing great reduction in vector size and obviating the harmful effects associated with whole viral proteins.

Chemokines are a large family of low molecular weight, inducible, secreted, proinflammatory cytokines which are produced by various cell types. They have been divided into several subfamilies on the basis of the positions of their conserved cysteines. The CXC family includes interleukin-8 (IL-8), growth regulatory gene, neutrophil-activating peptide-2, and platelet factor 4 (PF-4). Although IL-8 and PF-4 are both polymorphonuclear chemoattractants, angiogenesis is stimulated by IL-8 and inhibited by PF-4. The CC family includes monocyte chemoattractant protein-1 (MCP-1), RANTES (regulated on activation, normal T cell-expressed and secreted), macrophage inflammatory proteins (MIP-1α, MIP-1β, MIP-3β, MIP-1α), and eotaxin. MCP-1 is secreted by numerous cell types including endothelial, epithelial, and hematopoietic cells, and is a chemoattractant for monocytes and CD45RO+lymphocytes (Proost, P. (1996) Int. J. Clin. Lab. Res. 26: 211–223; Raport, C. J. (1996) J. Biol. Chem. 271: 17161–17166).

DNA sequences encoding chemokines such as MCP-1 (Yoshimura, et al., FEBS Lett. 244 487–93 1989; Rollins, et al., Mol. Cell Biol. 9 4687–95, 1989) and RANTES (Schall, et al., J. Immunol. 141 1018–25, 1988; and Nelson, et al., J. Immunol. 151 2601–12, 1993) and others are published and are found in the EMBL and NIH Genbank data bases.

The practice of the present invention employs conventional techniques of molecular biology, microbiology, recombinant DNA and immunology, within the skill of these arts. Such techniques are found in the scientific literature. (See, e.g., Brock, Biology of Microorganisms, Eighth Ed., (1997), (Madigan et al., eds.), Prentice Hall, Upper Saddle River, N.J.; Sambrook et al., Molecular Cloning: A Laboratory Manual, Second Ed., (1989); Oligonucleotide Synthesis, M. J. Gait Ed., 1984, Animal Cell Culture, Freshney, ed., 1987; Methods In Enzymology, series, Academic Press, Inc.; Gene Transfer Vectors for Mammalian Cells, Miller and Calos, Eds., 1987; Handbook of Experimental Immunology, Weir and Blackwell, Eds., Current Protocols in Molecular Biology, Ausubel et al., Eds., 1987 and Current Protocols in Immunology, Coligan et al., Eds., 1991)).

Genes of infectious agents may encode proteins that are antigenic (foreign antigens) in vertebrate hosts. Thus, such genes or fragments thereof are potentially useful for encoding immunogenic polypeptides of the methods described herein. The class of immunogenic polypeptides covered by the invention includes the class of epitope peptides. The invention will be efficacious with members of this class, whether already known or discovered in the future.

Similarly, although many genes of many infectious agents have been cloned and sequenced, others have not. Also, many tumor antigen genes, transplantation antigen genes, autoantigen genes, and genes for allergens have been identified and sequenced, but many others have not. It is intended that other genes identified, isolated and cloned in the future using methods known in the art for molecules having the desired functions (e.g. selected antigen or epitope genes) will be used in the present invention. All genes encoding selected immunogenic polypeptides in the cells and methods of the present invention are contemplated for use in the methods described herein.

Techniques for nucleic acid manipulation are well known. (See, e.g., Ausubel et al.; Ann. Rev. Biochem., 61:131–156 (1992)). Reagents useful in applying such techniques, such as restriction enzymes and the like, are widely known in the art and commercially available from a number of vendors.

Large amounts of the DNA expression vectors of the invention may be obtained using known procedures for molecular cloning and replication of the vector or plasmid carrying the sequences in a suitable host cell. DNA sequences encoding a desired protein, for example encoding an infectious agent antigen, can be assembled from cDNA fragments and oligonucleotide linkers, or from a series of oligonucleotides, to provide a synthetic infectious agent gene which can be expressed. Such sequences are preferably provided in the form of an open reading frame uninterrupted by internal nontranslated sequences or introns, which are typically present in eukaryotic genes. Genomic DNA containing the relevant sequences can also be used. Sequences of nontranslated DNA may be present 5' or 3' from the open reading frame, where such sequences do not interfere with manipulation or expression of the coding regions. Either complete gene sequences or partial sequences encoding desired antigenic peptides can be employed.

The nucleic acid sequences for use in the present invention may also be produced in part or in total by chemical synthesis, e.g. by the phosphoramidite method described by Beaucage and Carruthers, Tetra. Letts. 22:1859–1862 (1981), or the triester method (Matteucci et al., J. Am. Chem. Soc. 103:3185 (1981)), and may be performed on commercial automated oligonucleotide synthesizers. A double-stranded fragment may be obtained from the single-stranded product of chemical synthesis either by synthesizing the complementary strand and annealing the strand together under appropriate conditions, or by synthesizing the complementary strand using a DNA polymerase with an appropriate primer oligonucleotide.

The natural or synthetic nucleic acid fragments coding for a desired sequence may be incorporated into vectors capable of introduction into and replication in a prokaryotic or eukaryotic cell. Usually the vectors are suitable for replication in a unicellular host, such as yeast or bacteria, but may also be introduced into cultured mammalian or plant or other eukaryotic cell lines, with or without integration within the genome. The vectors will typically comprise an expression system recognized by the host cell, including the intended recombinant nucleic acid fragment encoding the desired polypeptide. The vectors will also contain a selectable marker, i.e. a gene encoding a protein needed for the survival or growth of a host cell transformed with the vector. The presence of this gene ensures the growth of only those host cells which express the inserted nucleic acid of interest. Typical selection genes encode proteins that 1) confer resistance to antibiotics or other toxic substances, e.g. ampicillin, neomycin methotrexate, etc.; b) complement auxotrophic deficiencies, or c) supply critical nutrients not available from complex media, e.g. the gene encoding D-alanine racemase for Bacilli. Other such markers include, for example, drug resistance genes such as hygromycin-B phosphotransferase (hph) which confers resistance to the antibiotic G418; the aminoglycoside phosphotransferase gene (neo or aph) from Tn5 which codes for resistance to the antibiotic G418; the dihydrofolate reductase (DHRF) gene; the adenosine deaminase gene (ADA) and the multi-drug resistance (MDR) gene. The choice of the proper selectable marker will depend on the host cell, and appropriate markers for different hosts are well known in the art. Such vectors may be prepared by means of standard recombinant techniques well known in the art (Sambrook et al., (1989); Ausubel et al., (1987)).

For gene transfer into the cells to express the selected molecules, nucleic acid may be directly introduced ex vivo in the form of "naked" nucleic acid, e.g. by microinjection, electroporation, as calcium-phosphate-DNA gels, nucleic acid particle "guns," with DEAE dextran, or in encapsulated form, e.g. in vesicles such as liposomes, or in a suitable viral vector.

Vectors containing the nucleic acid encoding the desired polypeptides are preferably recombinant expression vectors in which high levels of gene expression may occur, and which contain appropriate regulatory sequences for transcription and translation of the inserted nucleic acid sequence. Regulatory sequences refers to those sequences normally associated (e.g. within 50 kb) of the coding region of a locus which affect the expression of the gene (including transcription of the gene, and translation, splicing, stability or the like, of the messenger RNA). A transcriptional regulatory region encompasses all the elements necessary for transcription, including the promoter sequence, enhancer sequence and transcription factor binding sites. Regulatory sequences also include, inter alia, splice sites and polyadenylation sites. An internal ribosomal entry site (IRES) sequence may be placed between recombinant coding sequences to permit expression of more than one coding sequence with a single promoter.

In addition, operational elements may include leader sequences, termination codons, and other sequences needed or preferred for the appropriate transcription and subsequent translation of the inserted nucleic acid sequences. Secretion signals may also be included whether from a native protein, or from other secreted polypeptides of the same or related species, which permit the molecule to enter cell membranes, and attain a functional conformation.

It will be understood by one skilled in the art that the correct combination of expression control elements will depend on the recipient ("host") cells chosen to express the molecules. The expression vector should contain additional elements needed for the transfer and subsequent replication of the expression vector containing the inserted nucleic acid sequences in the host cells. Examples of such elements include, but are not limited to, origins of replication and selectable markers.

Suitable vectors for the invention may be plasmid or viral vectors, including adenoviruses, poxviruses, adenoassociated viruses (AAV), and retrovirus vectors (Price et al, Proc. Natl. Acad. Sci. USA 84:156–160 (1987) such as the MMLV based replication incompetent vector pMV-7 (Kirschmeier et al., DNA 7:219–225 (1988)). Plasmid expression vectors include plasmids including pBR322, pUC or Bluescript.TM. (Stratagene, San Diego, Calif.).

In retroviral vectors, genes are inserted so as to be under the transcriptional control of the promoter incorporated in the retroviral long terminal repeat (LTR), or by placing them under the control of a heterologous promoter inserted between the LTRs. This latter strategy provides a way of coexpressing a dominant selectable marker gene in the vector, thus permitting selection of cells that are expressing specific vector sequences.

Nonreplicating viral vectors can be produced in packaging cell lines which produce virus particles which are infectious but replication defective, rendering them useful vectors for introduction of nucleic acid into a cell lacking complementary genetic information enabling encapsidation (Mann et al. (1983), Cell 33:153; Miller and Buttimore (1986), Mol. Cell. Biol. 6:2895) (PA317, ATCC CRL9078). Packaging cell lines which contain amphotrophic packaging genes able to transduce cells of human and other species origin are preferred.

In general, nucleic acid encoding the selected molecules is inserted by standard recombinant DNA methods into a vector containing appropriate transcription and translation control sequences, including initiation sequences operably linked to the gene sequence to result in expression of the recombinant genes in the recipient host. Operably linked refers to a juxtaposition wherein the components are in a relationship permitting them to function in their intended manner. For instance, a promoter is operably linked to a coding sequence if the promoter effects its transcription or expression.

The nucleic acid sequences encoding the proteins or fragments thereof selected for expression are inserted in a single vector or in separate vectors. More than one gene encoding a selected immunogenic polypeptide, or portion thereof, may be inserted into an expression vector.

Genes to be introduced into such vectors include those encoding selected immunogenic polypeptides as described above, selected class I and class II HLA molecules, costimulation and other immunoregulatory molecules, ABC transporter proteins, including the TAP1 and TAP2 proteins, along with appropriate regulatory regions to drive expression of the recombinant coding sequences within recipient host cells. Thus, various combinations of coding sequences may be inserted in a suitable expression vector or vectors.

Sequences encoding selected immunogenic polypeptides, chemokine molecules and other immunoregulatory proteins will include at least a portion of the coding sequence sufficient to provide the engineered cell with the desired function. For example, in the case of a costimulation molecule, a portion of the coding sequence that enables it to bind its ligand on T cells can be used. Methods for determining such binding domains of molecules are known in the art. See, for example, Linsley et al., Proc. Natl. Acad. Sci. USA 87:5031–5035 (1990). Extracellular domains and transmembrane domains of costimulation molecules, as well as other immunoregulatory molecules, are preferably included.

With respect to the selected antigen, the antigen or antigens expressed by the vector will include portions of the antigen protein sufficient to permit recognition by the cells of the immune system, such as T cells, in the host.

It may be appreciated by one skilled in the art that use of recombinant DNA technologies can improve expression of transfected nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operably linking nucleic acid molecules to high-copy number plasmids, addition of vector stability sequences to plasmids, substitutions or modifications of transcription control signals (e.g., promoters, operators, enhancers), substitutions or modifications of translational control signals (e.g., ribosome binding sites, Kozak sequences, Shine-Dalgarno sequences), modification of nucleic acid molecules of the present invention to correspond to the codon usage of the host cell, and deletion of sequences that destabilize transcripts. The activity of an expressed recombinant protein of the present invention may be improved by fragmenting, modifying, or derivatizing nucleic acid molecules encoding such a protein.

DETAILED DESCRIPTION OF THE PREFERRED EMBODIMENTS

The present invention relates to a novel product and process for boosting the immune response of a mammalian host. It is now discovered that a composition comprising nucleic acid molecules encoding an immunopotentiating chemokine or fragment thereof can significantly enhance the immune response.

The present inventor has also discovered that DNA expression vectors that contain nucleic acid molecules encoding an immunogenic polypeptide or fragment thereof and an immunopotentiating chemokine or its fragment can act synergistically to produce a heightened immune response for effectively treating cancer and infectious disease. Thus, a mini-gene can be designed such that the insert size of the expression vector is reduced more than 10-fold which can still generate potent CTLs. This strategy has the potential to be developed into a vector encoding multiple epitopes for vaccination against viral infection. The present invention includes a pharmaceutical composition having at least two components: (a) an isolated nucleic acid molecule encoding an immunogenic polypeptide; and (b) an isolated nucleic acid molecule encoding a chemoldne. Administration of a pharmaceutical composition of the present invention to an animal results in the production of antigen and chemokine polypeptides. Each of the components of a pharmaceutical composition of the present invention is described in detail below, followed by a description of the methods by which the pharmaceutical composition is used and delivered.

One embodiment of the present invention is a DNA expression vector for inducing an immune response comprising a DNA sequence encoding an immunopotentiating chemokine or fragment thereof and a DNA sequence encoding at least one immunogenic protein or fragment thereof.

As will be apparent to one of skill in the art, the present invention is intended to apply to chemoldnes derived from all types of animals. Preferred animal from which to derive chemokines includes a mouse, a human and a dog. Particularly, preferred animals from which to derive chemokines include a dog and a human. An even more preferred animal from which to derive chemokines is a human.

According to the present invention, a chemokine-encoding nucleic acid molecule of the present invention is derived from the same species of animal as the animal to be treated. For example, a chemokine-encoding nucleic acid molecule derived from a canine (i.e., dog) nucleic acid molecule is used to treat a disease in a canine.

Further, the chemokine may be a chemokine that attracts T cells, a chemoline that attracts cells of the monocyte lineage, or a chemokine that attracts B cells. In a preferred embodiment of the invention, the chemokine is selected from the group consisting of MIP-1β, MIP-3β, MIP-1α, TCA-3, SDF-1, JE, Crg-2 and RANTES.

In another embodiment of the invention, the DNA expression vector described above further comprises one or more of the following nucleic acid sequences: (i) a DNA sequence encoding a hydrophobic leader signalling motif that directs the import of the immunogenic protein or fragment thereof into the endoplasmic reticulum of an antigen presenting cell, (ii) a DNA sequence encoding a signalling motif for retaining the immunogenic protein or fragment thereof within the endoplasmatic reticulum of an antigen presenting cell and (iii) a DNA sequence encoding a signalling motif for sending the helper epitope into the Class II pathways of an antigen presenting cell.

In a preferred embodiment of the invention, the immunogenic polypeptide is the gp120 IIIB coat protein of the HIV virus. In another embodiment of the invention, the immunogenic polypeptide is AG85A protein from the *Mycobacterium tuberculosis* (TB). In general, the immunogenic polypeptides to be expressed by the DNA expression vectors of the invention consist of one or more selected antigens or epitopes of an infectious agent or cancer, or of a transplantation antigen, allergen or autoantigen. Antigens or epitopes of an infectious agent include, but are not limited to, antigens or proteins encoded by the genomes of Hepadnaviridae including hepatitis B virus (HBV); Flaviviridae including human hepatitis C virus (HCV), yellow fever virus and dengue viruses; Retroviridae including human immunodeficiency viruses (HIV) and human T lymphotropic viruses (HTLV1 and HTLV2); Herpesviridae including herpes simplex viruses (HSV-1 and HSV-2), Epstein Barr virus (EBV), cytomegalovirus, varicella-zoster virus (VZV), human herpes virus 6 (HHV-6) human herpes virus 8 (HHV-8), and herpes B virus; Papovaviridae including human papilloma viruses; Rhabdoviridae including rabies virus; Paramyxoviridae including respiratory syncytial virus; Reovitidae including rotaviruses; Bunyaviridae including hantaviruses; Filoviridae including Ebola virus; Adenoviriidae; Parvoviridae including parvovirus B-19; Arenaviridae including Lassa virus; Orthomyxoviridae including influenza viruses; Poxviridae including Orf virus, molluscum contageosum virus and Monkey pox virus; Togaviridae; Coronaviridae including corona viruses; and Picornaviridae.

Particularly suitable infectious agent antigens are those which induce a T cell response, and particularly a CTL-response during infection. These may include, for example, from HBV, the core antigen, the E antigen and the surface antigen (HBsAg) (Okamoto et al., J. Gen. Virol. 67:1383–1389 (1986) (HBsAg from HBV)).

Non-viral organisms that are controlled by T cell immune responses include: pathogenic protozoa (e.g. *Pneumocystis carinii*, Trypanosoma, Leishmania, Plasmodia, and *Toxoplasma gondii*); bacteria (e.g., Mycobacteria, and Legioniella) and fungi (e.g. *Histoplasma capsulatum* and *Cocidioides immitus*).

These antigens are targets for therapy and/or prevention by the strategy described herein.

Cancer antigens for use in the invention include, but are not limited to, melanoma tumor antigens (Kawakami et al., Proc. Natl. Acad. Sci. USA 91:3515–3519 (1994); Kawakami et al., J. Exp. Med., 180:347–352 (1994); Kawakarni et al. Cancer Res. 54:3124–3126 (1994), including MART-1 (Coulie et al., J. Exp. Med. 180:35–42 (1991), gp100 (Wick et al., J. Cutan. Pathol. 4:201–207 (1988) and MAGE antigen, MAGE-1, MAGE-2 and MAGE-3 (Van der Bruggen et al., Science, 254:1643–1647 (1991)); CEA, TRP-1, P-15 and tyrosinase (Brichard et al., J. Exp. Med. 178:489 (1993)); HER-2/neu gene product (U.S. Pat. No. 4,968,603); estrogen receptor, milk fat globulin, p53 tumor suppressor protein (Levine, Ann. Rev. Biochem. 62:623 (1993)); mucin antigens (Taylor-Papdimitriou, International Pub. No. WO90/05142)); telomerases; nuclear matrix proteins; prostatic acid phosphatase; papilloma virus antigens; and antigens associated with the following cancers: melanomas, metastases, adenocarcinoma, thymoma, lymphoma, sarcoma, lung cancer, liver cancer, colon cancer, non-Hodgkins lymphoma, Hodgkins lymphoma, leukemias, uterine cancer, breast cancer, prostate cancer, ovarian cancer, cervical cancer, bladder cancer, kidney cancer, pancreatic cancer and others (e.g., Rosenberg, Ann. Rev. Med. 47:481–91 (1996).

Autoantigens for use as selected antigens include, but are not limited to, myelin basic protein; islet cell antigens; insulin; collagen and human collagen glycoprotein 39.

Transplantation antigens for use as selected antigens include, but are not limited to, different antigenic specificities of HLA-A, B and C Class I proteins. Different antigenic specificities of HLA-DR, HLA-DQ, HLA-DP and HLA-DW Class II proteins may also be used (WHO Nomenclature Committee, Immunogenetics 16:135 (1992); Hensen et al., in "Fundamental Immunology," ed. W. Paul, pp. 577–628, Raven Press, New York, 1993; and see NIH Genbank and EMBL data bases for HLA protein sequences).

Allergen antigens include, but are not limited to, environmental allergens such as dust mite allergens; plant allergens such as pollen, including ragweed pollen; insect allergens such as bee and ant venom; and animal allergens such as cat allergens.

The DNA expression vectors of the invention can be plasmids or viral vectors, including baculovirus vectors, adenovirus vectors, poxivirus vectors, adenoassociated virus vectors, and retrovirus vectors. In a preferred embodiment of the invention, the DNA expression vector is a plasmid selected from the group consisting of MIP-1β-SAK, MIP-1βSAO-YZLL, MIP-3β-SAK, MIP-3β-SAO-YZLL, MIP-1α-SAK, MIP-1α-SAO-YZLL, TCA-3-SAK, TCA-3-SAO-YZLL, SDF-1-SAK, SDF-1-SAO-YZLL, RANTES-SAK, ANTES-SAO-YZLL, JE-SAK, JE-SAO-YZLL, Crg-2-SAK, and Crg-2-SAO-YZLL.

| Peptide | SEQ ID NO: | Amino Acid Sequence |
|---|---|---|
| JE | 15 | Q P D A V N A P L T |
| TCA-3 | 16 | K S M L T V S N S |
| Crg-2 | 17 | I P L A R T V R |
| SDF-1 | 18 | K P V S L S Y R |
| MIP-3β | 19 | G A N D A E D |
| MIP-1α | 20 | A P Y G A D T P T A |
| RANTES | 21 | S P Y G S D T T P |
| MIP-1β | 22 | A P M G S D P P T S |

DNA expression vectors of the invention are constructed to contain DNA molecules encoding appropriate immunopotentiating chemokines, such as those shown in table above or variants thereof. The aforementioned preferred DNA expression vectors are derived from the Invitrogen pRc/CMV expression vector.

In one embodiment, a DNA molecule encoding a signal sequence of the invention is operably linked to a DNA molecule encoding a chemokine such that the signal sequence is expressed in the same reading frame of a polypeptide as the chemokine sequence. The chemokine sequence is likewise operably linked to an immunogenic sequence. SAK, in reference to plasmids or other expression vectors refers to the inclusion of a DNA molecule encoding an endoplasmic reticulum (ER) sequence. The SAK sequence is preferably operably linked to the carboxy-terminus of the immunogenic sequence. Such an arrangement of nucleic acid sequences in a DNA expression vector is illustrated in FIG. 2 (MIP-1β-SAK). In this case, the chemokine chosen is MIP-1β. The immunogenic peptide corresponds to that of HIV gp120 and a KDEL ER retention sequence is also included.

Generally, expression vectors are named for the individual nucleic acid sequence elements which are included in the vector. In FIGS. 10 through 15, CMV refers to the parent pRc/CMV vector. The vectors are further classified by the chemokine which is encoded by the vector. DNA sequences encoding the above-referenced peptide sequences (including fragments and variants thereof) can easily be determined by one of skill in the art. Particularly suitable chemokine sequences and abbreviations are listed in the above table.

The preferred vectors contain DNA sequences encoding one or more immunogenic polypeptides. In these examples, the chosen epitopes include gp120 (residues 315–329), a $T_c$ epitope, and OVA (317–342), a $T_h$ epitope. The sequences often include a hydrophobic leader sequence operably linked to the amino terminus of the chemokine encoding sequence (e.g., from about residue 50 to about residue 75 of the sequence of CMV/MIP-1β/p18/OVA/TMYZLL, SEQ ID NO: 3). TM in the context of DNA expression vectors refers to a transmembrane or membrane-spanning region. A suitable membrane spanning region is encoded, for example by the region from about residue 310 to about 370 of the sequence of CMV/MIP-1β/p18/OVA/TMYZLL (SEQ ID NO: 3). YZ in the context of DNA expression vector names refers to a YXXZ signal sequence targeting the endosome, while LL also indicates an endosome targeting sequence.

The CMV/Crg-2/SAK (FIGS. 14A and 14B) and CMV/RANES/SAK (FIGS. 15A and 15B) differ in that the DNA sequence for the Crg-2 sequence (SEQ ID NO:11) encodes the above-referenced Crg-2 chemokine peptide sequence (at residues 99–123 of SEQ ID NO:11), while that encoding the RANTES peptide contains a sequence from residues 99–123 encoding the peptide disclosed as SEQ ID NO:17. These plasmids may be cut at the ApaI or other suitable restriction endonuclease site for the introduction of DNA sequences encoding immunogenic polypeptides and other sequences of the invention.

Another embodiment of the present invention is a method to treat an animal with cancer or infectious diseases, the method comprising administering to an animal an effective amount of a pharmaceutical composition comprising: (a) a nucleic acid sequence encoding a chemokine or fragment thereof; and (b) a nucleic acid sequence encoding an immunogenic polypeptide or fragment thereof, in which the nucleic acid molecules are operably linked to one or more transcription control sequences, and in which the pharmaceutical composition is targeted to the site of a cancer.

In another embodiment of the present invention, a pharmaceutical composition further comprises a pharmaceutically acceptable carrier. As used herein, a "carrier" refers to any substance suitable as a vehicle for delivering a nucleic acid molecule of the present invention to a suitable in vivo or in vitro site. As such, carriers can act as a pharmaceutically acceptable excipient of a pharmaceutical composition containing a nucleic acid molecule of the present invention. Preferred carriers are capable of maintaining a nucleic acid molecule of the present invention in a form that, upon arrival of the nucleic acid molecule to a cell, the nucleic acid molecule is capable of entering the cell and being expressed by the cell. Carriers of the present invention include: (1) excipients or formularies that transport, but do not specifically target a nucleic acid molecule to a cell (referred to herein as non-targeting carriers); and (2) excipients or formularies that deliver a nucleic acid molecule to a specific site in an animal or a specific cell (i.e., targeting carriers). Examples of non-targeting carriers include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- and o-cresol, formalin and benzyl alcohol. Preferred auxiliary substances for aerosol delivery include surfactant substances non-toxic to an animal, for example, esters or partial esters of fatty acids containing from about six to about twenty-two carbon atoms. Examples of esters include, caproic, octanoic, lauric, palmitic, stearic, linoleic, linolenic, olesteric, and oleic acids. Other carriers can include metal particles (e.g., gold particles) for use with, for example, a biolistic gun through the skin. Pharmaceutical compositions of the present invention can be sterilized by conventional methods and/or lyophilized.

Targeting carriers are herein referred to as "delivery vehicles." Delivery vehicles of the present invention are capable of delivering a pharmaceutical composition of the present invention to a target site in an animal. A "target site" refers to a site in a host to which one desires to deliver a pharmaceutical composition. For example, a target site can be a cancer cell, a tumor, or a lesion caused by an infectious agent, or an area around such cell, tumor or leasion, which is targeted by direct injection or delivery using liposomes or other delivery vehicles. Examples of delivery vehicles include, but are not limited to, artificial and natural lipid-containing delivery vehicles. Natural lipid-containing delivery vehicles include cells and cellular membranes. Artificial lipid-containing delivery vehicles include liposomes and micelles. A delivery vehicle of the present invention can be modified to target to a particular site in an animal, thereby targeting and making use of a nucleic acid molecule of the present invention at that site. Suitable modifications include manipulating the chemical formula of the lipid portion of the delivery vehicle and/or introducing into the vehicle a compound capable of specifically targeting a delivery vehicle to a preferred site, for example, a preferred cell type. Specifically targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. For example, an antibody specific for a receptor or protein found on the surface of a cancer cell can be introduced to the outer surface of a liposome delivery vehicle so as to target the delivery vehicle to the cancer cell. Tumor cell ligands include ligands capable of binding to a molecule on the surface of a tumor cell. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

Liposomes are a preferred delivery vehicle of the present invention. Limposomes are capable of remaining stable in an animal for a sufficient amount of time to deliver a nucleic acid molecule of the present invention to a preferred site in the animal. In the present invention, the liposomes are preferably stable in the animal into which they have been admninistered for at least about 30 minutes, more preferably for at least about 1 hour and even more preferably for at least about 24 hours.

Liposomes of the present invention comprises a lipid composition that is capable of targeting a nucleic acid molecule of the present invention to a particular, or selected, site in an animal. Preferably, the lipid composition is capable of targeting to any organ of an animal, more preferably to the lung, liver, spleen, heart brain, lymph nodes and skin of an animal, and even more preferably to the lung of an animal.

The lipid composition is also capable of fusing with the plasma membrane of the targeted cell to deliver a nucleic acid molecule into a cell. Preferably, the transfection efficiency is about 0.5 microgram ($\mu$g) of DNA per 16 nanomole (nmol) of liposome delivered to about $10^6$ cells, more preferably about 1.0 $\mu$g of DNA per 16 nmol of liposome delivered to about $10^6$ cells, and even more preferably about 2.0 $\mu$g of DNA per 16 nmol of liposome delivered to about $10^6$ cells.

Preferred liposome of the present invention are between about 100 and 500 nanometers (nm), more preferably between about 150 and 450 nm and even more preferably between about 200 and 400 nm in diameter.

Suitable liposomes for use with the present invention include essentially any liposome. Preferred liposomes include liposomes standardly used in, for example, gene delivery methods known to those of skill in the art. More preferred liposomes comprise a polycationic lipid composition and/or liposomes having a cholesterol backbone conjugated to polyethylene glycol.

In one embodiment, liposomes of the present invention comprise a compound capable of targeting the liposome to a tumor cell. Such liposomes preferably include a tumor cell ligand exposed on the outer surface of the liposome.

Complexing liposomes with a nucleic acid molecule of the present invention can be achieved using methods standard in the art. A suitable concentration of a nucleic acid molecule of the present invention to add to liposomes includes a concentration effective for delivering a sufficient amount of nucleic acid molecule to a cell such that the cell can produce sufficient immunogenic polypeptide and/or cytokine protein to regulate effector cell immunity in a desired manner. Preferably, from about 0.1 $\mu$g to about 10 $\mu$g of nucleic acid molecule of the present invention is combined with about 8 nmol liposomes, more preferably from about 0.5 $\mu$g to about 5 $\mu$g of nucleic acid molecule is combined with about 8 nmol liposomes, and even more preferably about 1.0 $\mu$g of nucleic acid molecule is combined with about 8 nmol liposomes.

Another preferred delivery vehicle comprises a recombinant virus particle vaccine. A recombinant virus particle vaccine of the present invention includes a pharmaceutical composition of the present invention, in which the nucleic acid sequences contained in the composition are packaged in a viral coat that allows entrance of DNA into a cell so that the DNA is expressed in the cell. A number of recombinant virus particles can be used, including, but not limited to, those based on alphaviruses, poxviruses, adenoviruses, herpesviruses, arena virus and retroviruses.

Another preferred delivery vehicle comprises a recombinant cell vaccine. Preferred recombinant cell vaccines of the present invention include tumor vaccines, in which allogeneic (i.e., cells derived from a source other than a patient, but that are histiotype compatible with the patient) or autologous (i.e., cells isolated from a patient) tumor cells are transfected with nucleic acid sequences contained in a pharmaceutical composition, irradiated and administered to a patient by, for example, intradermal, intravenous or subcutaneous injection. Pharmaceutical compositions to be administered by tumor cell vaccine, include nucleic acid sequences of the present invention without carrier. Tumor cell vaccine treatment is useful for the treatment of both tumor and metastatic cancer. Use of a tumor vaccine of the present invention is particular useful for treating metastatic cancer, including preventing metastatic disease, as well as, curing existing metastatic disease. Methods for developing and administering include those standard in the art (see for example, Dranoff et al., Proc. Natl. Acad. Sci. USA 90:3539–3543, 1993).

A pharmaceutical composition of the present invention is useful for the treatment of a variety of diseases, including, but not limited to, cancer, autoimmune disease, infectious diseases, and other diseases that can be alleviated by either stimulating or suppressing T cell activity. A pharmaceutical composition of the present invention is advantageous for the treatment of cancer in that the composition overcomes the mechanisms by which cancer cells avoid immune elimination (i.e., by which cancer cells avoid the immune response effected by the animal in response to the disease). Cancer cells can avoid immune elimination by, for example, being only slightly immunogenic, modulating cell surface antigens and inducing immune suppression. A suitable pharmaceutical composition for use in the treatment of cancer comprises a combination of a immunogenic polypeptide-encoding recombinant molecule and a chemokine-encoding recombinant molecule of the present invention. A more preferred pharmaceutical composition for use in the treatment of cancer comprises a combination of a immunogenic polypeptide-encoding recombinant molecule and a chemokine-encoding recombinant molecule of the present invention combined (separately or together) with a delivery vehicle, preferably a liposome, such as disclosed herein. A pharmaceutical composition of the present invention, upon entering targeted cells, leads to the production of immunogenic polypeptide and chemokine that activate cytotoxic T cells, natural killer cells, T helper cells and macrophages. Such cellular activation overcomes the otherwise relative lack of immune response to cancer cells, leading to the destruction of such cells.

A pharmaceutical composition of the present invention is useful for the treatment of cancers, both tumors and metastatic forms of cancer. Treatment with the pharmaceutical composition overcomes the disadvantages of traditional treatments for metastatic cancers. For example, compositions of the present invention can target dispersed metastatic cancer cells that cannot be treated using surgical methods. In addition, administration of such compositions do not result in the harmful side effects caused by chemotherapy and radiation therapy.

A pharmaceutical composition of the present invention is preferably used to treat cancers, including, but not limited to, melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, primary hepatic cancers, lung cancers, pancreatic cancers, gastrointestinal cancers, renal cell carcinomas, hematopoietic neoplasias, leukemias and lymphomas. Particularly preferred cancers to treat with a pharmaceutical composition of the present invention, include melanomas, lung cancers, thyroid carcinomas, breast cancers, renal cell carcinomas, squamous cell carcinomas, brain tumors and skin cancers. A pharmaceutical composition of the present invention is useful for treating tumors that can form in such cancers, including malignant and benign tumors.

A pharmaceutical composition of the present invention is particularly useful for the treatment of infectious diseases caused by pathogens, including, but not limited to, intracellular bacteria (i.e., a bacteria that resides in a host cell), internal parasites, pathogenic fungi and endoparasites. Particularly preferred infectious diseases to treat with a pharmaceutical composition of the present invention include tuberculosis, leprosy, aspergillosis, coccidioidomycosis, cryptococcoses, leishmaniasis and toxoplasmosis.

In order to treat an animal with disease, a pharmaceutical composition of the present invention is administered to the animal in an effective manner such that the composition is capable of treating that animal from disease. For example, a recombinant molecule, when administered to an animal in an effective manner, is able to stimulate effector cell immunity in a manner that is sufficient to alleviate the disease afflicting the animal. According to the present invention, treatment of a disease refers to alleviating a disease and/or preventing the development of a secondary disease resulting from the occurrence of a primary disease. An effective administration protocol (i.e., administering a pharmaceutical composition in an effective manner) comprises suitable dose parameters and modes of administration that result in treatment of a disease. Effective dose parameters and modes of administration can be determined using methods standard in the art for a particular disease. Such methods include, for example, determination of survival rates, side effects (i.e., toxicity) and progression or regression of disease. In particular, the effectiveness of dose parameters and modes of administration of a pharmaceutical composition of the present invention when treating cancer can be determined by assessing response rates. Such response rates refer to the percentage of treated patients in a population of patients that respond with either partial or complete remission. Remission can be determined by, for example, measuring tumor size or microscopic examination for the presence of cancer cells in a tissue sample.

In accordance with the present invention, a suitable single dose size is a dose that is capable of treating an animal with disease when administered one or more times over a suitable time period. Doses can vary depending upon the disease being treated. In the treatment of cancer, a suitable single dose can be dependent upon whether the cancer being treated is a primary tumor or a metastatic form of cancer. Doses of a pharmaceutical composition of the present invention suitable for use with direct injection techniques can be used by one of skill in the art to determine appropriate single dose sizes for systemic administration based on the size of an animal. A suitable single dose of a pharmaceutical composition to treat a tumor is a sufficient amount of a immunogenic polypeptide-encoding recombinant molecule and a chemokine-encoding recombinant molecule to reduce, and preferably eliminate, the tumor following transfection of the nucleic acid sequences into cells at or near the tumor site. A preferred single dose of the immunogenic polypeptide-encoding recombinant molecule is an amount that, when transfected into a target cell population leads to the production of from about 250 femtograms (fg) to about 1 $\mu$g, preferably from about 500 fg to about 500 picogram (pg), and more preferably from about 1 pg to about 100 pg of immunogenic polypeptide per transfected cell. A preferred single dose of a chemokine-encoding recombinant molecule is an amount that when transfected into a target cell population leads to the production of from about 10 pg to about 1 $\mu$g, preferably from about 100 pg to about 750 pg, and more preferably about 500 pg of cytokine per transfected.

A suitable single dose of a immunogenic polypeptide-encoding recombinant molecule and a chemokine-encoding recombinant molecule in a non-targeting carrier to administer to an animal to treat a tumor, is an amount capable of reducing, and preferably eliminating, the tumor following transfection of the nucleic acid sequences into cells at or near the tumor site. A preferred single dose of a pharmaceutical composition to treat a tumor is from about 100 μg to about 2 milligrams (mg) of total nucleic acid sequences, more preferably from about 150 μg to about 1 mg of total nucleic acid sequences, and even more preferably from about 200 μg to about 800 μg of total nucleic acid sequences. A preferred single dose of a immunogenic polypeptide-encoding recombinant molecule complexed with liposomes, is from about 100 μg of total DNA per 800 nmol of liposome to about 2 mg of total nucleic acid sequences per 16 micromole (μmol) of liposome, more preferably from about 150 μg per 1.2 μmol of liposome to about 1 mg of total nucleic acid sequences per 8 μmol of liposome, and even more preferably from about 200 μg per 2 μmol of liposome to about 400 μg of total nucleic acid sequences per 3.2 μmol of liposome.

A preferred single dose of a chemokine-encoding recombinant molecule in a non-targeting carrier to administer to an animal to treat a metastatic cancer, is from about 100 μg to about 4.0 mg of total nucleic acid sequences, more preferably from about 150 μg to about 3 mg of total nucleic acid sequences, and even more preferably from about 200 μg to about 2 mg of total nucleic acid sequences. A preferred single dose of a chemokine-encoding recombinant molecule complexed with liposomes to administer to an animal to treat a metastatic cancer, is from about 100 μg of total nucleic acid sequences per 800 nmol of liposome to about 4.0 mg of total nucleic acid sequences per 32 μmol of liposome, more preferably from about 200 μg per 1.6 μmol of liposome to about 3 mg of total nucleic acid sequences per 24 μmol of liposome, and even more preferably from about 400 μg per 3.2 μmol of liposome to about 2 μg of total nucleic acid sequences per 16 μmol of liposome.

According to the present invention, a single dose of a pharmaceutical composition useful to treat a lesion, comprising a immunogenic polypeptide-encoding recombinant molecule in a non-targeting carrier or liposomes, respectively, and a chemokine-encoding recombinant molecule in a non-targeting carrier or liposomes, respectively, is substantially similar to those doses used to treat a tumor (as described in detail above).

It will be obvious to one of skill in the art that the number of doses administered to an animal is dependent upon the extent of the disease and the response of an individual patient to the treatment. For example, a large tumor may require more doses than a smaller tumor. In some cases, however, a patient having a large tumor may require fewer doses than a patient with a smaller tumor, if the patient with the large tumor responds more favorably to the pharmaceutical composition than the patient with the smaller tumor. Thus, it is within the scope of the present invention that a suitable number of doses includes any number required to cause regression of a disease. A preferred protocol is monthly administrations of single doses (as described above) for up to about 1 year. A preferred number of doses of a pharmaceutical composition comprising a immunogenic polypeptide-encoding recombinant molecule and a chemokine-encoding recombinant molecule in a non-targeting carrier or complexed with liposomes in order to treat a tumor is from about 1 to about 10 administrations per patient, preferably from about 2 to about 8 administrations per patient, and even more preferably from about 3 to about 5 administrations per person. Preferably, such administrations are given once every 2 weeks until signs of remission appear, then once a month until the disease is gone.

A preferred number of doses of a pharmaceutical composition comprising an immunogenic polypeptide-encoding recombinant molecule and a chemokine-encoding recombinant molecule in a non-targeting carrier or complexed with liposomes in order to treat a metastatic cancer, is from about 2 to about 10 administrations patient, more preferably from about 3 to about 8 administrations per patient, and even more preferably from about 3 to about 7 administrations per patient. Preferably, such administrations are given once every 2 weeks until signs of remission appear, then once a month until the disease is gone.

According to the present invention, the number of doses of a pharmaceutical composition to treat a lesion comprising an immunogenic polypeptide-encoding recombinant molecule and a chemokine-encoding recombinant molecule, in a non-targeting carrier or liposomes, respectively, is substantially similar to those number of doses used to treat a tumor (as described in detail above).

A pharmaceutical composition is administered to an animal in a fashion to enable expression of the administered recombinant molecule of the present invention into a curative protein in the animal to be treated for disease. A pharmaceutical composition can be administered to an animal in a variety of methods including, but not limited to, local administration of the composition into a site in an animal, in which the site contains abnormal cells or pathogens to be destroyed (e.g., injection locally within the area of a tumor or a lesion); and systemic administration.

Pharmaceutical compositions to be delivered by local administration include: (a) nucleic acid sequences of the present invention in a non-targeting carrier (e.g., as "naked" DNA molecules, such as is taught, for example in Wolff et al., 1990, Science 247, 1465–1468); and (b) nucleic acid sequences of the present invention complexed to a delivery vehicle of the present invention. Suitable delivery vehicles for local administration comprise liposomes. Delivery vehicles for local administration can further comprise ligands for targeting the vehicle to a particular site (as described in detail herein).

A preferred method of local administration is by direct injection. Direct injection techniques are particularly useful for the treatment of disease by, for example, injecting the composition into a mass formed by abnormal cells or a granuloma mass induced by pathogens. Preferably, a recombinant molecule of the present invention complexed with a delivery vehicle is administered by direct injection into or locally within the area of a tumor mass, a granuloma mass or a cancer cell. Administration of a composition locally within the area of a mass or a cell refers to injecting the composition centimeters and preferably, millimeters within the mass or the cell. A preferred tumor mass to inject includes discrete inner body and cutaneous solid tumors. A preferred inner body tumor to inject includes a discrete solid tumor that forms in the brain, breast, liver, kidney, colon, prostate, testicular, ovary, spleen and/or lymph node. A preferred cutaneous tumor to inject includes a discrete solid melanoma.

Another method of local administration is to contact a pharmaceutical composition of the present invention in or around a surgical wound. For example, a patient can undergo surgery to remove a tumor. Upon removal of the tumor, the pharmaceutical composition can be coated on the surface of tissue inside the wound or the composition can be injected into areas of tissue inside the wound. Such local administration is useful for treating cancer cells not excised by the surgical procedure, as well as, preventing recurrence of the primary tumor or development of a secondary tumor in the area of the surgery.

Preferred methods of systemic administration, include intravenous or intradermal injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA 189:11277–11281, 1992, which is incorporated herein by reference in its entirety). Oral delivery can be performed by complexing a pharmaceutical composition of the present invention to a carrier capable of withstanding degradation by digestive enzymes in the gut of an animal. Examples of such carriers, include plastic capsules or tablets, such as those known in the art. Topical delivery can be performed by mixing a pharmaceutical composition of the present invention with a lipophilic reagent (e.g., DMSO) that is capable of passing into the skin.

Pharmaceutical compositions of the present invention can be administered to any animal, preferably to mammals and birds, and more preferably to humans, house pets, economic produce animals and zoo animals. Economic produce animals include animals to be consumed or that produce useful products (e.g., sheep for wool production). Zoo animals include those animals harbored in zoos. Preferred animals to protect include humans, dogs, cats, sheep, cattle, horses and pigs, with humans and dogs being particularly preferred. While a pharmaceutical composition of the present invention is effective to treat disease in inbred species of animals, the composition is particularly useful for treating outbred species of animals, in particular those having tumors.

As an alternative to DNA expression vectors, protein molecules encoded by these vectors can be introduced into the host for inducing an immune response in all of the emodiments described above. Thus, all of the effects claimed above for the DNA expression vectors of the present invention can be obtained by direct injection of polypeptides encoded by such the DNA expression vectors of the invention.

The present invention also includes pharmaceutical products for all of the uses contemplated in the methods described herein. For example, a pharmaceutical product comprising pure plasmid DNA vector or formulations thereof, operatively coding for an immunogenic polypeptide or peptide, may be prepared in physiologically acceptable administrable form. The pharmaceutical product may be placed in a container, with a notice associated with the container in the form prescribed by a governmental agency regulating the manufacture, use or sale of pharmaceuticals, which notice is reflective of approval by the agency of the form of the DNA for human administration. Such notice, for example, may be labeling approved by the United States Food and Drug Administration (USFDA) or the approved product insert.

In order that this invention may be more fully understood, the following examples are set forth. These examples are for the purpose of illustration only and are not to be construed as limiting the scope of the invention in anyway.

EXAMPLES

These experiments were aimed at enhanced generation of CTLs specific for the HIV gp120 (316–325) sequence. In designing the mini-gene for expression by a vector, the subcellular localization of the mini-gene product is directed by utilizing signalling motifs, which are amino acid sec (aiences contained within proteins for directing the location of proteins within the cell. A hydrophobic leader sequence was chosen to direct the import of the mini-protein into the ER (Gierasch, L. M; Biochemistry 28:923–930 (1989)) and a KDEL sequence (SEQ ID NO:23) (lys-asp-glu-leu) (Pelham, H. R .B.; Annu. Rev. Cell Biol. 5:1–23(1989); Teasdale, R. D. and M. R. Jackson; Annu. Rev. Cell Dev. Biol. 12:27–54 (1996)) for the retention of the mini-protein within the ER (FIG. 1A) have been incorporated. The inclusion of the chemokine sequence from MIP-1β into the construct is shown in FIG. 1B. The nucleotide sequence is given in FIG. 2.

The gene chosen as a model to study is the gp120 IIIB coat protein of the HIV virus which has been the focus of many efforts in vaccine development. The peptide from this protein which is recognized by CTL in BALB/c mice has previously been demonstrated to lie within the region of 15 amino acids 315–329, specifically residues 318–327 (Takahashi, H.; et al.; Proc. Natl. Acad. Sci USA 95:3105–3109 (1988)). Additional adjacent residues to ensure the correct processing of the mini-gene product by the cell are included.

A vector encoding the first ten amino acids of the murine chemokine, macrophage inflammatory protein-1β (MIP-1β) was constructed. The presence of this sequence significantly improves the ability of the plasmid to induce specific cytotoxic T lymphocytes to the HIV gp120 sequence. In FIG. 2, the sequence encoded in the pRc/CMV vector (Invitrogen, San Diego, Calif.) is presented.

DNA was injected into mice using the procedure outlined below, and a $^{51}$Cr-release assay was used to monitor its effects. In this assay, target cells, presenting HIV epitope, are labeled with $^{51}$Cr-sodium chromate and are then incubated with lymphocytes from the spleens of injected animals. If specific CTLs are present, they kill the target cells resulting in the release of radioactivity into the medium for detection by gamma counting.

This plasmid (designated MIP-1β-SAK) and the control plasmid (without the MIP-1β sequence, SAK) were purified using Qiagen columns and cesium chloride banding. 100–200 μg DNA in 100 μl PBS were injected i.d. into each BALB/c-H-2dm2 mouse. After two weeks each mouse was boosted with the same dose of DNA by the same route. There were 3 mice per group. After a further two weeks, the mice were sacrificed and their spleen cells were stimulated with 1 μM HIV gp120 peptide (SEQ ID NO:24: RGPGRAFVTI) for 5 days. Their cellular immune response as measured by the presence of specific cytotoxic T cells, was determined in a standard 4 hour $^{51}$Cr-release assay. Target cells for this assay were P815, incubated with either the gp120 peptide (SEQ ID NO:24) or a control peptide (labelled Mpi) SEQ ID NO:25: KGPDKGNEF), and labeled with $^{51}$Cr-sodium chromate. After 4 hours, 100 μL supernatant was counted on a gamma counter and percentage specific lysis was calculated.

It was found that the SAK construct generated a moderate response. However, the MIP-1β-SAK construct gave an excellent response, shown in FIG. 3. The summary of these experiments is shown in FIG. 4.

Similar experiments were performed to test the efficacy of other chemokines for potentiating the immune response. In particular, as FIGS. 5, 6 and 7 show, constructs that included encoding sequences for the chemokines, T cell activation gene (TCA-3) and Stromal cell-derived factor-1 (SDF-1) gave an enhanced immune response compared to constructs with no chemokine encoding sequence.

Similar experiments were performed by including sequences encoding for the various chemokines in a SAO-YZLL construct as opposed to a SAK construct. FIG. 9 compares the MIP-1β-SAK plasmid to a MIP-1β-SAO-YZLL plasmid. The immune response results for the MIP- 1β-SAO-YZLL plasmid were similar to the MIP-1β-SAK plasmid. Therefore, it is to be expected that other expression vectors similarly constructed will yield similar results.

Similar results are to be expected if the chemokine sequence in the preceding plasmids is replaced with a sequence encoding (i) the chemokine JE, which is a ligand for the CCR2 receptor and activator of monocytes and naive T cells, (ii) the chemokine cytokine response gene-2 (Crg-2), which is a ligand for CXCR-3, a receptor on activated T cells, preferentially expressed on the $T_{H1}$ subset, (iii) the chemokine macrophage inflammatory protein-3β (MIP-3β), (iv) the chemokine macrophage inflammatory protein-1α (MIP-1α) or (v) the chemokine regulated on activation, normal T cell-expressed and secreted (RANTES).

It is also to be appreciated that the foregoing description of the invention has been presented for purposes of illustrations and explanation and is not intended to limit the invention to the precise compositions and manner of practice herein. It is to be appreciated therefore, that changes may be made by those skilled in the art without departing from the spirit of the invention.

What is claimed is:

1. A DNA expression vector for inducing an immune response comprising:

a first DNA sequence encoding an immunopotentiating chemokine fragment comprising the sequence of SEQ ID NO:22, said fragment having a length that is not more than 10% of the source immunopotentiating chemokine; and a second DNA sequence encoding a heterologous immunogenic polypeptide.

2. The DNA expression vector of claim 1 wherein the immunopotentiating chemokine fragment is a chemokine fragment that attracts T cells.

3. The DNA expression vector of claim 1 wherein the immunopotentiating chemokine fragment is a chemokine fragment that attracts cells of the monocyte lineage.

4. The DNA expression vector of claim 1 wherein the immunopotentiating chemokine fragment is a chemokine fragment that attracts B cells.

5. The DNA expression vector of claim 1 wherein the DNA expression vector further comprises a third DNA sequence encoding a hydrophobic leader signalling motif that directs the import of the immunogenic polypeptide into the endoplasmic reticulum of an antigen presenting cell.

6. The DNA expression vector of claim 5 wherein the DNA expression vector further comprises a fourth DNA sequence encoding a signalling motif for retaining the immunogenic polypeptide within the endoplasmic reticulum of an antigen presenting cell.

7. The DNA expression vector of claim 6 wherein the DNA expression vector further comprises a fifth DNA sequence encoding a signalling motif for sending the immunogenic polypeptide into the MHC Class II pathways of an antigen presenting cell.

8. The DNA expression vector of claim 1 wherein the immunogenic polypeptide is the gp120 IIIB coat protein of the HIV virus.

9. The DNA expression vector of claim 1 wherein the immunogenic polypeptide is the AG85A protein from the *Mycobacterium tuberculosis*.

10. The DNA expression vector of claim 1 wherein the DNA expression vector is selected from the group consisting of plasmids, adenovirus vectors, poxivirus vectors, adenoassociated virus vectors, and retrovirus vectors.

11. The DNA expression vector of claim 10 wherein the vector comprises the sequence of SEQ ID NO:1 or SEQ ID NO:3.

12. The DNA expression vector of claim 1 wherein the immunogenic polypeptide is a cytotoxic T lymphocyte epitope.

13. The DNA expression vector of claim 1 wherein the immunogenic polypeptide is a B cell epitope.

14. The DNA expression vector of claim 12 further comprising a sequence encoding a T helper cell epitope.

15. The DNA expression vector of claim 13 further comprising a sequence encoding a T helper cell epitope.

16. A composition for inducing an immune response comprising:

an effective amount of the DNA expression vector of claim 1 and a carrier.

17. A method of manufacturing a composition for inducing an immune response comprising:

combining an effective amount of the DNA expression vector of claim 1 and a carrier.

* * * * *

UNITED STATES PATENT AND TRADEMARK OFFICE
CERTIFICATE OF CORRECTION

PATENT NO.    : 6,562,800 B1
DATED         : May 13, 2003
INVENTOR(S)   : Minnie McMillan It is certified that error appears in the above-identified patent and that said Letters Patent is hereby corrected as shown below:

Column 1,
Line 18, insert the following before the section entitled BACKGROUND OF THE INVENTION:

-- STATEMENT REGARDING FEDERALLY SPONSORED RESEARCH OR DEVELOPMENT
This invention was made with United States government support under Contract No. R01 NS 33822 awarded by the National Institute of Health. The government has certain rights in this invention. --

Signed and Sealed this

Ninth Day of December, 2003

JAMES E. ROGAN
*Director of the United States Patent and Trademark Office*